(12) United States Patent
Kiser et al.

(10) Patent No.: US 8,814,778 B2
(45) Date of Patent: Aug. 26, 2014

(54) PERICARDIAL DEVICES, SYSTEMS AND METHODS FOR OCCLUDING AN ATRIAL APPENDAGE

(75) Inventors: Andy Christopher Kiser, West End, NC (US); Mark Douglas Landers, Pinehurst, NC (US)

(73) Assignee: AtriCure, Inc., West Chester, OH (US)

( * ) Notice: Subject to any disclaimer, the term of this patent is extended or adjusted under 35 U.S.C. 154(b) by 313 days.

(21) Appl. No.: 13/151,403

(22) Filed: Jun. 2, 2011

(65) Prior Publication Data

US 2012/0035622 A1 Feb. 9, 2012

Related U.S. Application Data

(63) Continuation-in-part of application No. 12/456,855, filed on Jun. 23, 2009.

(60) Provisional application No. 61/351,043, filed on Jun. 3, 2010.

(51) Int. Cl.
A61B 1/04 (2006.01)
A61B 17/12 (2006.01)
A61B 17/128 (2006.01)
A61B 17/00 (2006.01)

(52) U.S. Cl.
CPC ....... *A61B 17/12013* (2013.01); *A61B 17/1285* (2013.01); *A61B 2017/00243* (2013.01); *A61B 2017/00557* (2013.01); *A61B 2017/12018* (2013.01)
USPC ............................ 600/104; 600/109; 600/101

(58) Field of Classification Search
USPC ......................................... 600/101, 104, 109
See application file for complete search history.

(56) References Cited

U.S. PATENT DOCUMENTS

| 4,817,634 A | 4/1989 | Holleman et al. |
| 5,327,909 A | 7/1994 | Kiser et al. |
| 6,893,442 B2 | 5/2005 | Whayne |
| 7,063,698 B2 | 6/2006 | Whayne et al. |

(Continued)

FOREIGN PATENT DOCUMENTS

WO   WO 2007/127664 A1   11/2007

OTHER PUBLICATIONS

Abashian et al., "Effect of Ablation on Local Activation Intervals and Dominant Frequencies of Fibrillation," Computers in Cardiology, 2007; 34:781-783.

(Continued)

*Primary Examiner* — Carl H Layno
*Assistant Examiner* — Jon Eric C Morales
(74) *Attorney, Agent, or Firm* — Kilpatrick Townsend & Stockton LLP

(57) ABSTRACT

Disclosed are devices for pericardial access to the heart, including direct access to the left atrium. In certain embodiments, the device may comprise a device and/or an atrial appendage (AA) portal having a configuration such that the distal end of the device and/or the portal can access an atrial appendage while the proximal end of the device and/or portal can extend to outside of the subject. The devices and methods may also include a pericardial portal for emplacement of the device and/or the AA portal. Also, methods for using such devices and/or AA portals and pericardial portals to perform surgery on the heart, and systems (e.g., kits) comprising these devices and/or portals in combination with other therapeutic devices are disclosed.

59 Claims, 15 Drawing Sheets

(56) References Cited

U.S. PATENT DOCUMENTS

| | | | |
|---|---|---|---|
| 7,410,487 | B2 | 8/2008 | Whayne |
| 7,463,932 | B2 | 12/2008 | Cawthra, Jr. |
| 2002/0049457 | A1* | 4/2002 | Kaplan et al. .................. 606/139 |
| 2003/0158563 | A1 | 8/2003 | McClellan |
| 2004/0127967 | A1 | 7/2004 | Osypka |
| 2006/0004388 | A1 | 1/2006 | Whayne et al. |
| 2006/0020162 | A1 | 1/2006 | Whayne et al. |
| 2006/0200124 | A1 | 9/2006 | Whayne et al. |
| 2006/0206113 | A1 | 9/2006 | Whayne et al. |
| 2006/0235381 | A1 | 10/2006 | Whayne et al. |
| 2006/0293646 | A1 | 12/2006 | Whayne et al. |
| 2006/0293740 | A1 | 12/2006 | Heil, Jr. et al. |
| 2007/0043351 | A1 | 2/2007 | Fleischman et al. |
| 2007/0083082 | A1 | 4/2007 | Kiser et al. |
| 2007/0083225 | A1 | 4/2007 | Kiser et al. |
| 2007/0249991 | A1 | 10/2007 | Whayne et al. |
| 2007/0250058 | A1 | 10/2007 | Whayne et al. |
| 2008/0114288 | A1 | 5/2008 | Whayne et al. |
| 2008/0114342 | A1 | 5/2008 | Whayne et al. |
| 2008/0114354 | A1 | 5/2008 | Whayne et al. |
| 2008/0114355 | A1 | 5/2008 | Whayne et al. |
| 2008/0243119 | A1 | 10/2008 | Whayne |
| 2009/0024213 | A1 | 1/2009 | Raman et al. |
| 2010/0160725 | A1* | 6/2010 | Kiser et al. .................... 600/104 |

OTHER PUBLICATIONS

Beaufort-Krol et al., "Comparison of Longevity, Pacing, and Sensing Characteristics of Steroid-Eluting Epicardial versus Conventional Endocardial pacing Leads in Children," J. Thorac. Cardiovasc. Surg. 1999; 117:523-528.

Budde et al., "Robot-assisted 13 MHz epicardial ultrasound for endoscopic quality assessment of coronary anastomoses," Interactive Cardiovascular and Thoracic Surgery 2004; 3:616-620.

Cohen et al., "Permanent Epicardial Pacing in Pediatric Patients Seventeen Years of Experience and 1200 Outpatient Visits," Circulation 2001; 103:2585-2590.

Covidian, web page available at http://www.covidien.com/autosuture/pagebuilder.aspx?topicID=7407&breadcrumbs=0:122497,131955:0,309:0.

Kiser et al., "Achieving Metrics during Beating Heart Ex-Maze Procedures Improve Outcomes," Heart Surg. Forum, 2008; 11(4): E237-E242.

Kiser et al., "Blunt Tracheobronchial Injuries: Treatment and Outcomes," Ann. Thorac Surg., Jun. 2001: 71(6):2059-2065.

Kiser et al., "Evaluation of a Novel Epicardial Atrial Fibrillation Treatment System," Ann Thorac Surg., Jan. 2008; 85(1): 300-304.

Kiser et al., "MPB: Clinical Evaluation of the Extra-Cardiac Maze (Ex-Maze) Procedure," Innovations, 2007, vol. 2, No. 3: 129.

Kiser et al., "Presentation Number: VI3—Paracardioscopic Ex-Maze Procedure for Atrial Fibrillation," Innovations, 2008, vol. 3, No. 2: 117-118.

Kiser, "In Their Own Words—The College's Chapter Visit Program: Becoming involved in the Political Process," Bull Am Coll Surg., Oct. 2000; 85(10):19-20.

Milano et al., "Transmyocardial holmium laser revascularization: feasibility of a thoracoscopic approach," European Journal of Cardio-Thoracic Surgery 1998; 14:105-110.

Robicsek, "Minimally Invasive MIDCABG and TMLR," Ann. Thorac. Surg. 1999; March;67(3):892.

Spittell et al., "Venous Complications After Insertion of a Transvenous Pacemaker," Mayo Clin. Proc. 1992; 67(3):258-265.

Bailey et al., "Abstract 2865: Short Term Results of the Convergent Endo-Epicardial Ablation Procedure for the Treatment of Long Standing Persistent Atrial Fibrillation," Circulation, 2009; 120:S707.

Dumas et al., "Abstract 3102: Translesion Myocardial Impedance as an Indicator of Lesion Production by RF Ablation," Circulation, 2006; 114:II_654-II_655.

Dumas et al., "Myocardial electrical impedance as a predictor of the quality of RF-induced linear lesions," Physiol Meas., Oct. 2008; 29(10): 1195-1207, Epub Sep. 18, 2008.

Himel et al., "Translesion stimulus-excitation delay indicates quality of linear lesions produced by radiofrequency ablation in rabbit hearts," Circulation, 2006; 114:II_352.

Himel et al., "Translesion stimulus-excitation delay indicates quality of linear lesions produced by radiofrequency ablation in rabbit hearts," Physiol. Meas., 2007, 28: 611-623.

Kiser et al., "Lung Retrieval from Non-Heart Beating Cadavers with the Use of a Rat Lung Transplant Model," J Thorac Cardiovasc Surg., Jul. 2001; 122(1): 18-23.

Kiser et al., "Metastatic Melanoma to the Pleural Space," Ann Thorac Surg., Oct. 2002; 74(4): 1257.

Kiser et al., "Pacemakers and Intraoperative Cardiac Interactions: Implications for Surgeons," Bull Am Coll Surg., Mar. 2000; 85(3): 18-20.

Kiser et al., "Paracardioscopic Creation of a Comprehensive Biatrial Lesion Pattern During Minimally Invasive Atrial Fibrillation Treatment," J. Am. Coll. Cardiol., Mar. 2008: 51:A12; 1008-115.

Kiser et al., "Primary Percutaneous Endoscopic Button Gastrostomy: A Modification of the "Push" Technique," J. Am . Coll. Surg., Jun. 1999; 188(6): 704-706.

Kiser et al., "Spontaneous Hemopneumothorax in Women," South Med. J., Dec. 2000; 93(12): 1209-1211.

Kiser et al., "The Surgeon at Work: Subcutaneous Injection of Donor Sites for Split-Thickness Skin Grafts," J. Am. Coll. Surg., Mar. 1996; 182(3): 265-267.

Kiser et al., "Totally Extracardiac Maze Procedure Performed on the Beating Heart," Ann Thorac Surg., Nov. 2007; 84(5): 1783-1785.

Kiser, "Paracardioscopy Provides Endoscopic Visualization of the Heart," Innovations, Jul./Aug. 2009; vol. 4, No. 4: 233-235.

Blackshear et al., "Appendage obliteration to reduce stroke in cardiac surgical patients with atrial fibrillation," Ann Thorac Surg., Feb. 1996; 61(2):755-9.

Edgerton., "Total thoracoscopic ablation of atrial fibrillation using the Dallas lesion set, partial autonomic denervation, and left atrial appendectomy," Operative Techniques in Thorac. and Cardiovasc Surg., 2009;14:224-242.

Rodriguez et al., "Minimally invasive bi-atrial cryomaze operation for atrial fibrillation," Operative Techniques in Thorac and Cardiovasc Surg., 2009;14:208-223.

\* cited by examiner

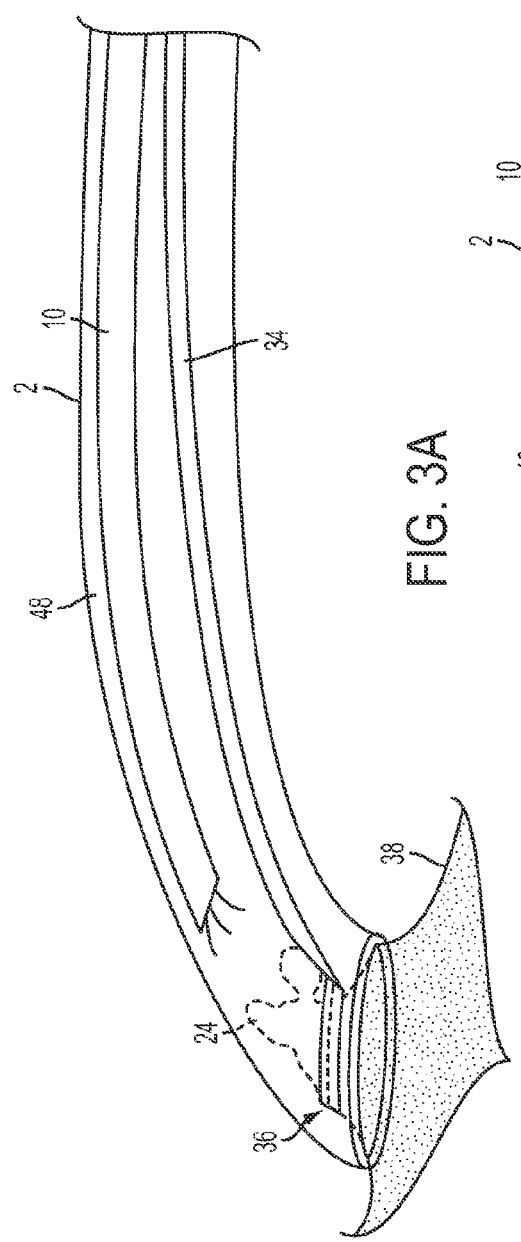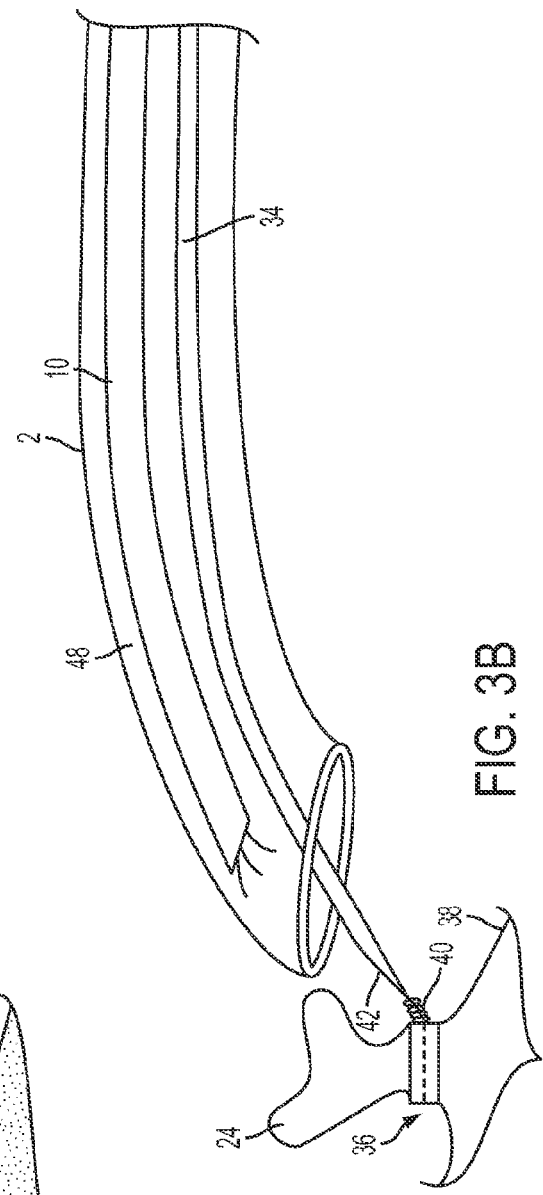

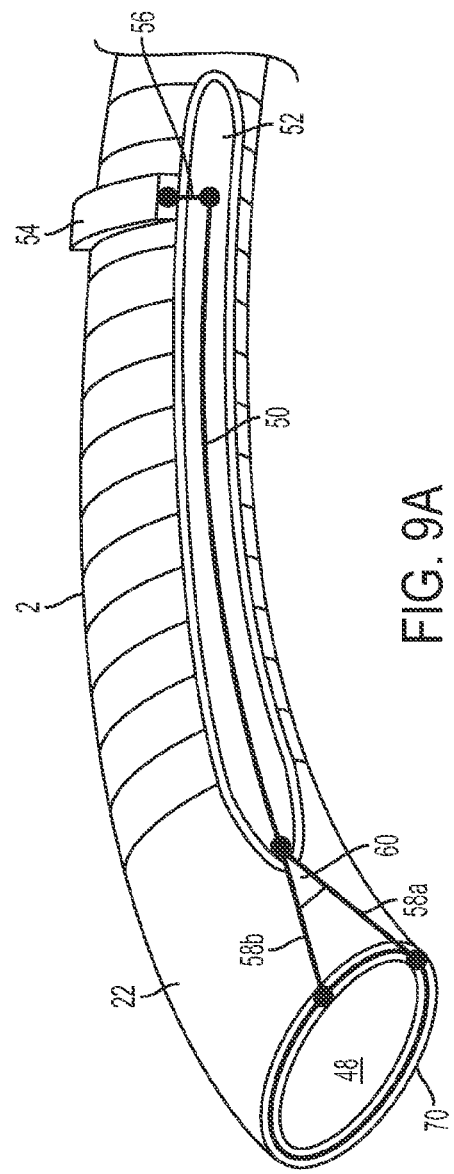
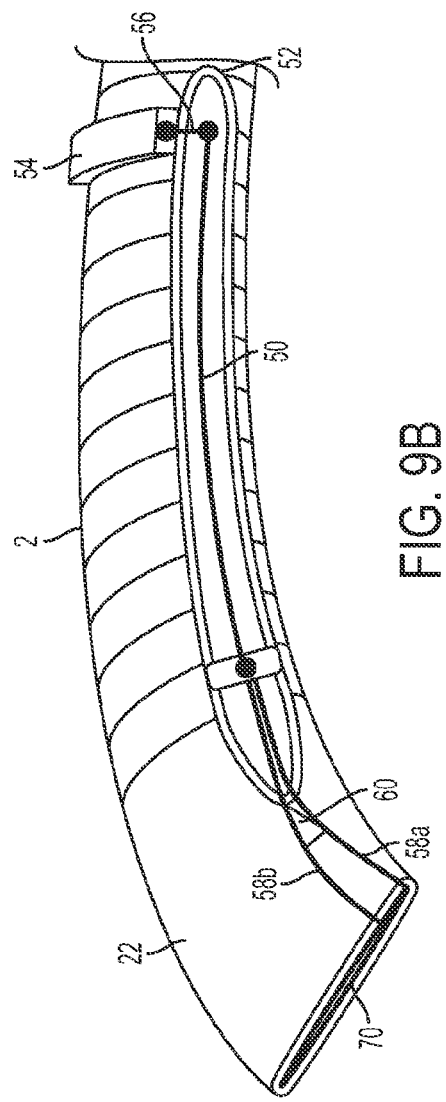
FIG. 9A
FIG. 9B

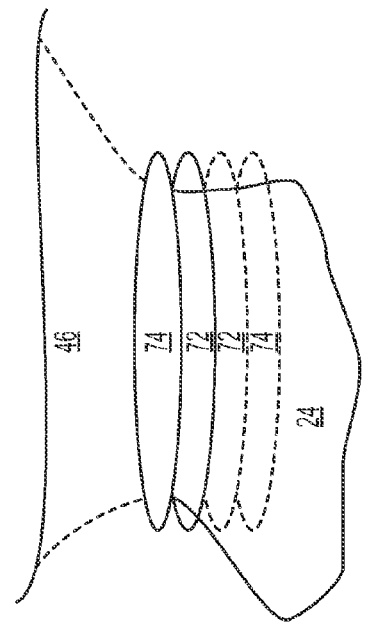
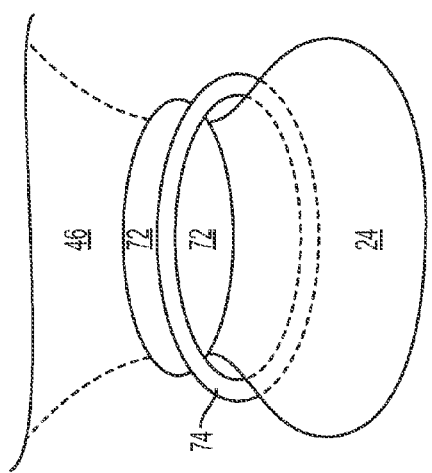
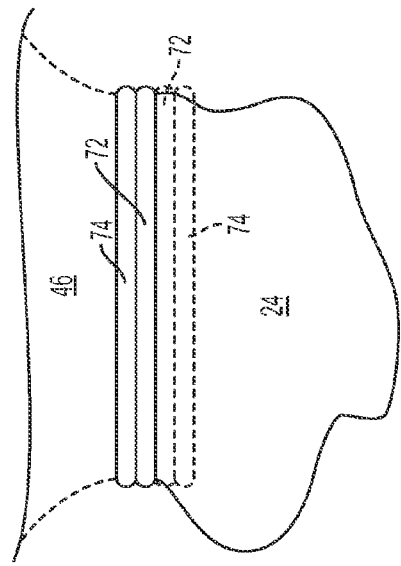
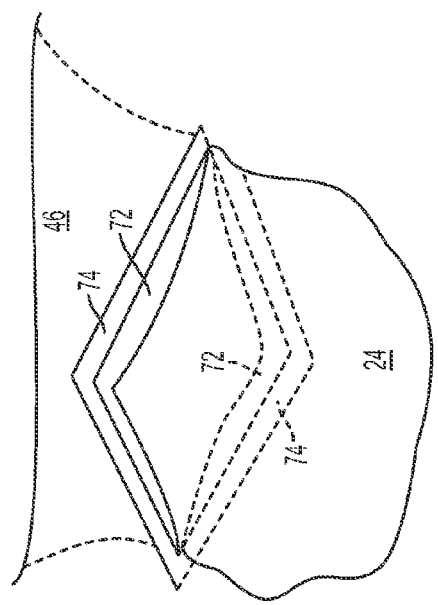

PERICARDIAL DEVICES, SYSTEMS AND METHODS FOR OCCLUDING AN ATRIAL APPENDAGE

RELATED APPLICATIONS

This application claims priority to U.S. Provisional Application No. 61/351,043 filed Jun. 3, 2010 and is a continuation-in-part of U.S. patent application Ser. No. 12/456,855, filed Jun. 23, 2009. The disclosure of U.S. Provisional Application No. 61/351,043 and U.S. patent application Ser. No. 12/456,855 are incorporated by reference in their entireties herein.

FIELD OF THE INVENTION

The present invention relates to devices, systems and methods for pericardial access, visualization, and exclusion and/or removal of an atrial appendage.

Atrial Appendage Therapies

For patients with isolated atrial fibrillation (AF), the left atrial appendage (LAA) may be the source of embolic events, such as stroke and heart attack (Blackshear J L and Odell J A, Appendage obliteration to reduce stroke in cardiac surgical patients with atrial fibrillation, Ann. Thorac. Surg., 1996; 61:755-759). Many physicians feel that exclusion or ligation of the LAA is indicated for patients with AF to reduce this risk. The less invasive Percutaneous Left Atrial Appendage Transcatheter Occlusion (PLAATO) device and the Watchman Device (Atritech; Plymouth, Minn.) have been designed to exclude the LAA from circulation and thus, reduce embolic events. The device can be placed inside the heart at the base of the left atrial appendage through a defect created in the atrial septum with a catheter in the femoral vein, a large vein in the groin. Although minimally invasive, the procedure can be technically challenging and may leave a compromised communication between the left and right atrium. Surgeons often exclude the LAA during cardiac surgical procedures in patients with atrial fibrillation. However, for those patients with isolated atrial fibrillation who do not require sternotomy for cardiac surgery, a less invasive surgical exclusion is desirable.

Methods have been described which utilize mini-thoracotomy or thoracoscopic access to surgically exclude or remove the LAA during procedures to treat atrial fibrillation. Techniques described include removal or exclusion of the LAA from inside the left atrium while the heart is arrested during cardiopulmonary bypass (Rodriguez E, Cook R C, Chu M W A, and Chitwood W R, Jr., Minimally invasive bi-atrial cryomaze operation for atrial fibrillation, Operative Techniques in Thorac and Cardiovasc Surg., 2009; 14:208-223), and amputation of the LAA while the heart is beating using an endoscopic stapler (Edgerton J R., Total thoracoscopic ablation of atrial fibrillation using the Dallas lesion set, partial autonomic denervation, and left atrial appendectomy, Operative Techniques in Thorac. and Cardiovasc Surg., 2009; 14:224-242). New devices have been developed to enable less invasive LAA exclusion (e.g., the Cosgrove-Gillinov Left Atrial Appendage Occlusion System, Atricure, West Chester, Ohio; and the Cardioblate Closure Left Atrial Appendage Occlusion Device, Medtronic, Minneapolis, Minn.). Clinical investigation is underway for these devices.

Direct access and visualization of the LAA has required painful incisions in the chest which often delay recovery. Access to the LAA with pericardial visualization is now possible via a subxyphoid or transdiaphragmatic approach. The pericardium is a tough, fibrous sac, filled with fluid, and that surrounds the heart. This sac allows free movement of the heart while it is beating. The sac can enlarge over time if too much pericardial fluid is generated or if the heart enlarges. The sac can also become inflamed and attach to the surface of the heart due to surgery, infection, or malignancy.

Pericardioscopy, or paracardioscopy, relates to accessing the heart within the pericardial sac using endoscopic techniques. The development of pericardioscopy (U.S. patent application Ser. No. 12/456,855 incorporated herein by reference) has enabled similar "keyhole" procedures for diseases of the chest but without the use of robotics. Pericardioscopy may use a device which is positioned via a surgical defect (opening) in the diaphragm into the pericardial space. Alternatively, access to, and visualization within, the pericardium using a device through an incisions beneath the xyphoid is an acceptable procedure. The device can create a temporary space within the pericardium, between the heart and the pericardial sac, where visualization, manipulation, and procedures can be performed on the heart surface.

For example, pericardioscopy may be used to treat atrial fibrillation (AF) and atrial flutter. In this procedure, a cannula may be used to access the outside of the heart via the pericardial sac. Then, an ablation device may be juxtaposed against the epicardial surface at specific locations to thereby scar (i.e., ablate) the heart tissue in such a manner so as to short-circuit any electrical activity (fibrillations) occurring in the heart. Pericardioscopy provides the direct visualization and the direct access to the epicardial surface of the heart vital to the totally endoscopic treatment of AF (Kiser et al., Innovations 2008; 3:117).

While methods and devices that use pericardial procedures are available for treatment of atrial fibrillation (AF), there is a need to develop devices and procedures such that pericardial or subxyphoid access to the heart can be used in other procedures. There is also a need to develop devices and procedures such that other organs in the thoracic cavity can be accessed and treated endoscopically. Thus, the present invention comprises pericardial-based devices, systems or methods for ligation of an atrial appendage, including the LAA.

SUMMARY

Embodiments of the present invention comprise endoscopic devices, systems and methods for occluding an atrial appendage via pericardial access to the heart. The method may be embodied in a variety of ways.

In certain embodiments, the invention comprises a device for performing a surgical procedure on an atrial appendage, wherein at least a portion of the device is configured for insertion of at least a portion of the atrial appendage into a portion of the device and configured to exclude and/or remove an atrial appendage from an atrium to which the appendage is attached.

Yet other embodiments of the present invention comprise methods to access an atrial appendage of a heart in a subject via a pericardial approach so as to perform a surgical procedure upon the atrial appendage. The method may comprise the steps of inserting a portion of portal comprising a device for performing a surgical procedure on an atrial appendage into the pericardium of the subject, wherein at least a portion of the device is configured for insertion of at least a portion of the atrial appendage into a portion of the device and configured to exclude and/or remove an atrial appendage from an atrium to which the appendage is attached, and wherein the portal comprises a proximal end having an opening and a distal end having an opening and a lumen connecting the proximal and distal openings; manipulating the proximal end of the portal to position the distal opening of the portal at or near the surface of the atrium; and inserting at least a portion of the atrial appendage into the device or the portion of the device.

The present invention also comprises systems for occluding or removing an atrial appendage. For example, the system may comprise a device for tying off an atrial appendage, and an AA portal and/or a pericardial portal. In an embodiment, the invention comprises a system for tying off an atrial appendage comprising a device for performing a surgical procedure on an atrial appendage via a pericardial approach, wherein at least a portion of the device is configured for insertion of at least a portion of the atrial appendage into a portion of the device and configured to exclude and/or remove an atrial appendage from an atrium to which the appendage is attached and a portal for positioning the device in close proximity to the atrial appendage.

The present invention may be better understood by reference to the following non-limiting description.

BRIEF DESCRIPTION OF THE FIGURES

FIG. 3, panels A-B, illustrates the exclusion of an AA with a felt reinforced lasso of suture placed at the base of the AA under direct visualization using an AA portal in accordance with an embodiment of the present invention. Panel A shows the suture within the AA portal and loose around the base of the LAA, panel B illustrates the felt and suture tightened at the proper location for exclusion.

FIG. 11, panels A-D, illustrates clips positioned around an atrial appendage in accordance with various embodiments of the invention where panels A and B show an oval distal band/clip positioned around an atrial appendage where panel A shows the clip open, and panel B shows the clip closed around the atrial appendage, and panels C and D show a diamond-shaped clip positioned around an atrial appendage where panel C shows the clip open, and panel D shows the clip closed around the atrial appendage.

DETAILED DESCRIPTION

Figure 1:
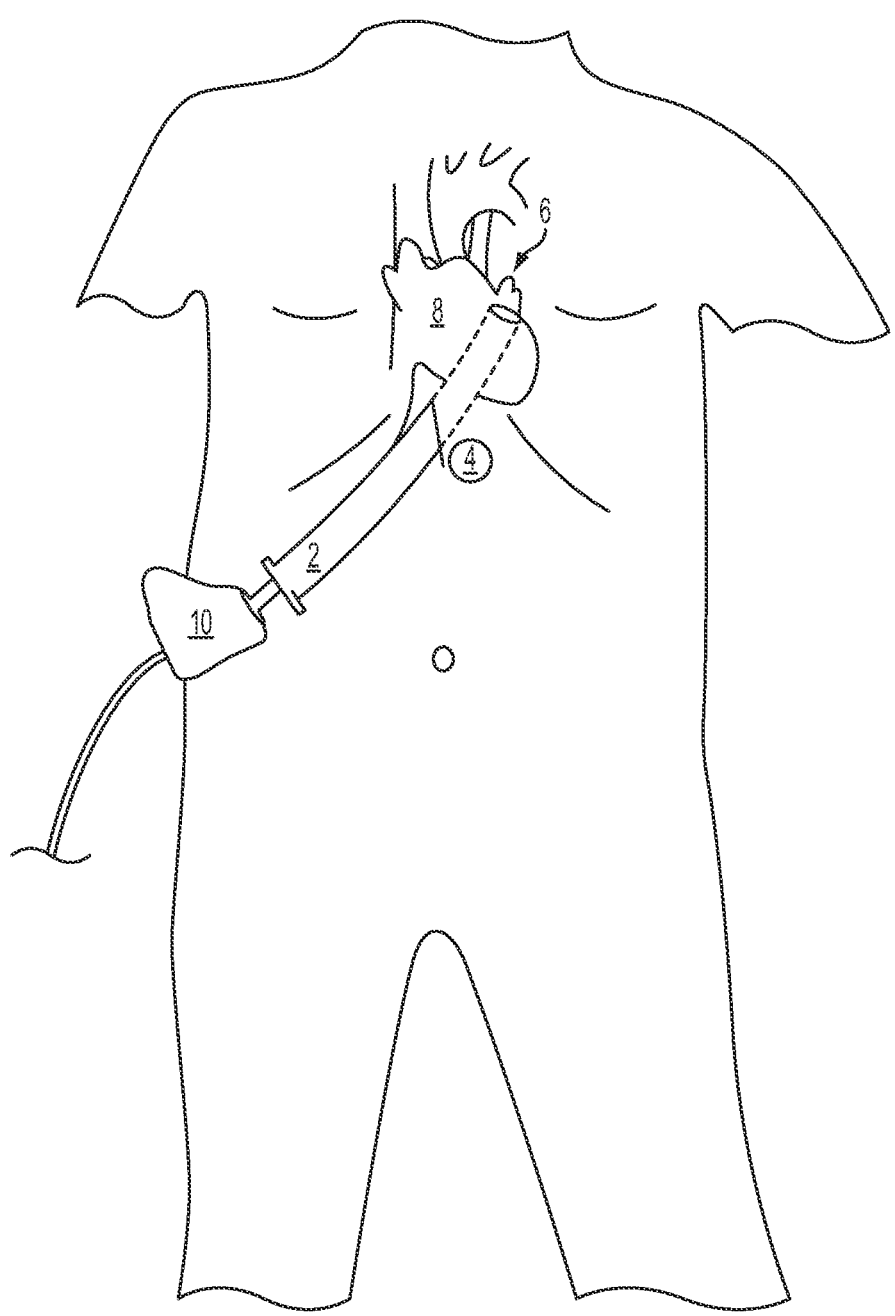
FIG. 1 illustrates insertion of an atrial appendage (AA) portal or outer pericardial portal via a transdiaphragmatic subxyphoid approach with the portal and endoscope passing from external to the body, through the incision and into the pericardial sac towards the left atrial appendage (LAA), in accordance with an embodiment of the present invention.

Embodiments of the invention comprise pericardial-based atrial appendage (AA) exclusion devices, systems and methods of use of such devices and systems.

In various embodiments of the devices of the invention, an atrial appendage (AA) portal or a pericardial portal may be used to access the atrial appendage.

As used herein, a pericardial portal is an access member configured to provide access to the pericardium from an incision made in a subject, and having a distal opening and a proximal opening and a lumen that connects the distal opening and the proximal opening. Thus, the portal is generally long enough to access the pericardium from an incision (e.g., subxyphoid) but has a circumference that is minimized so as to reduce trauma to the subject. A pericardioscopic portal is a pericardial portal that includes an endoscope.

As used herein, an atrial appendage (AA) portal is an access member configured to provide access to the atrial appendage from an incision made in a subject, and having a distal opening and a proximal opening and a lumen that connects the distal opening and the proximal opening. Thus, like the pericardial portal, the AA portal is generally long enough to access the pericardium from an incision (e.g., subxyphoid) and has a circumference that is minimized so as to reduce trauma to the subject. Generally, the AA portal and the pericardial portal are similar in configuration, except that the AA portal is configured to access an atrial appendage, and so may be smaller in diameter than a pericardial portal. In some cases, the AA portal and the pericardial portal are used together, such that the pericardial portal is used to access the pericardium, and the AA portal is used either singly, or inserted within the lumen of the pericardial portal, to access the atrial appendage. An AA portal may also include an endoscope.

In an embodiment, the AA portal and/or the pericardial portal is a cylinder. In certain embodiments, the AA portal and/or the pericardial portal is a cannula. In certain embodiments, the AA portal and/or the pericardial portal is a tube. In certain embodiments, the AA portal and/or the pericardial portal is an oval cylinder. In certain embodiments, the AA portal is a rectangular tube. Or, in certain embodiments, the device to be used in conjunction with the pericardial portal comprises an round cylinder, an oval cylinder or a rectangular tube.

As described in more detail herein, the AA portal may comprise a single portal and/or may be used in conjunction with a second, outer cannula or portal, such as a pericardial portal. For example, in certain embodiments, the device may comprise an outer pericardial portal for delivering the AA portal to an atrial appendage. Or, the pericardial portal may be used with a device that can occlude an atrial appendage, but that is not an atrial appendage portal.

As used herein, "distal" refers to the end of a device that is furthest from the operator (e.g., physician). "Proximal" refers to the end of a device that is closest to the operator. For example, the "distal" end of a cannula or portal is the end inserted into a patient and the "proximal" end is the end that is outside of the patient and that can be maneuvered by a physician.

Also, as used herein, the terms "expandable" and/or "expandable/contractible" are used interchangeably to denote a material that can expand and/or contract from a first position to a second position. Such materials may be made of an elastic type material and/or have elastic properties.

Thus, in certain embodiments, the invention comprises a device for performing a surgical procedure on an atrial appendage, wherein at least a portion of the device is configured for insertion of at least a portion of the atrial appendage into a portion of the device and configured to exclude and/or remove an atrial appendage from an atrium to which the appendage is attached. In an embodiment, the device comprises a portal comprising a proximal end having an opening and a distal end having an opening and a lumen connecting the proximal and distal openings, wherein the distal end is configured for insertion of at least a portion of the atrial appendage into a portion of the device. In an embodiment, the distal end of the device and/or the portal can access an atrial appendage while the proximal end of the device and/or portal can extend to outside of the subject.

In certain embodiments, and as described in more detail herein, the distal end of the device is curvilinear such that the distal end is not parallel to the longitudinal axis of the device.

In certain embodiments and as described in more detail herein, the device for performing a procedure on the atrial appendage is configured to be inserted into a pericardial portal, the pericardial portal comprising a proximal end having an opening and a distal end having an opening and a lumen connecting the proximal and distal openings. Also, in certain embodiments the portal may comprising a cannula comprising a proximal end having an opening and a distal end having an opening and a lumen connecting the proximal and distal openings. In some embodiments, the device may be used with an endoscope.

In certain embodiments, suction can be applied to create a seal between at least a portion of the distal opening of the device and at least part of the atrial appendage. Also, in certain embodiments the device may comprise a soft material at the distal end.

The device for occluding the atrial appendage may, in certain embodiments comprise a tying band configured to be tied around a portion of the atrial appendage. In certain embodiments, at least a portion of the tying band comprises a material designed to cushion the tying band.

In other embodiments, the device for occluding the atrial appendage may comprise an expandable and/or contractible band positioned on or near the distal end. In some embodiments, the device may further comprise an inflatable member positioned on the distal end. The device may also, in certain embodiments, comprise a lumen configured to inflate the inflatable member.

The inflatable member may be used to facilitate positioning of the expandable and/or contractible band on the atrial appendage. For example, in certain embodiments, the expandable and/or contractible band is positioned proximal to the inflatable member such that when the inflatable member is inflated, the band is secured on the distal end of the device, and when the inflatable member is deflated, the band can be urged over the deflated inflatable member so as to be released from the distal end of the device. Alternatively, in other embodiments, the expandable and/or contractible band is positioned substantially on top of the inflatable member, such that when the inflatable member is deflated, the band is secured on the distal end of the device, and when the inflatable member is inflated, the band is pushed off the distal end of the device.

The device may comprise a contractible end that can be used to clamp the atrial appendage. For example, in certain embodiments, the distal end of the device is sufficiently flexible so as to be collapsed around the end of an atrial appendage.

Additionally and/or alternatively, the device may comprise a clip and/or band positioned at the distal end, and which may be positioned around an atrial appendage so as to occlude the atrial appendage from the remainder of the atrium. The clip and/or band may be shaped to have at least two longer sides and two shorter sides such that when the clip and/or band is closed around the atrial appendage, the longer sides flatten the appendage in a manner so as to substantially avoid plication of the appendage. For example, in alternate embodiments, the clip or band is oval, rectangular or diamond in shape. Also in certain embodiments, the clip and/or band is releasably engaged with the distal end of the device, such that when the clip and/or band is collapsed around an atrial appendage, the clip or band may be released from the end of the device so as to collapse around at least a portion of the atrial appendage.

In certain embodiments, the distal end of the device is shaped to collapse around an atrial appendage without the application of force. In certain embodiments, the device comprises a mechanism to open the distal end. For example, in certain embodiments, the mechanism to open the distal end of the portal and/or the device comprises at least one bar that when urged distally, pushes the distal end of the portal and/or the device from a naturally closed configuration to an open configuration. In certain embodiments, the clip and/or band is releasably engaged with the distal end, such that when the clip and/or band is collapsed around an atrial appendage, the clip or band may be released from the end of the device so as to collapse around at least a portion of the atrial appendage.

For each of the embodiments, of the devices, methods and systems, the device may be configured specifically to access either the left atrial appendage or the right atrial appendage.

Yet other embodiments of the present invention comprise methods to access an atrial appendage of a heart in a subject via a pericardial approach so as to perform a surgical procedure upon the atrial appendage. The method may comprise the steps of inserting a portion of portal comprising a device for performing a surgical procedure on an atrial appendage into the pericardium of the subject, wherein at least a portion of the device is configured for insertion of at least a portion of the atrial appendage into a portion of the device and configured to exclude and/or remove an atrial appendage from an atrium to which the appendage is attached, and wherein the portal comprises a proximal end having an opening and a distal end having an opening and a lumen connecting the proximal and distal openings; manipulating the proximal end of the portal to position the distal opening of the portal at or near the surface of the atrium; and inserting at least a portion of the atrial appendage into the device or the portion of the device.

In certain embodiments, the portal comprises an atrial appendage portal comprising a proximal end having an opening and a distal end having an opening and a lumen connecting the proximal and distal openings, wherein the distal end is configured for insertion of at least a portion of the atrial appendage into a portion of the device.

In certain embodiments, the method comprises inserting the device and/or the atrial portal into an outer pericardial portal and positioning the distal opening of the atrial appendage portal at the surface of the atrium. Also, in certain embodiments, at least a portion of the distal end of the device and/or the portal(s) is curvilinear such that the distal opening is not parallel to the longitudinal axis of the device. The method may also comprise using an endoscope to provide an image of body structures present near the distal end of the portal(s). Also, in certain embodiments, the portal(s) and/or the device comprises a soft material surrounding the distal end of the portal and/or the device.

Also, in certain embodiments, the method further comprises applying a vacuum to an inner lumen of the portal (e.g., atrial appendage portal or pericardial portal) or the device to encourage the atrial appendage into at least a portion of the device or the portal and/or to create a seal between the distal opening of the device and at least part of the atrial appendage.

In certain embodiments, the method may comprise positioning a device to exclude and/or remove an atrial appendage at the distal end of the atrial appendage portal and/or the pericardial portal.

A variety of devices may be used to occlude the atrial appendage in the methods of the invention. In an embodiment, the device comprises a tying band configured to be tied around a portion of the atrial appendage. In certain embodiments, the tying band comprises a suture. In certain embodiments, at least a portion of the suture comprises a material designed to cushion the suture. For example, the method may comprise providing the tying band at the distal opening of the portal, using the tying band to encircle at least a portion of the atrial appendage, and tightening the tying around the atrial appendage to exclude the atrial appendage from the atrium to which the appendage is attached.

In other embodiments, the device comprises an expandable and/or contractible band and/or clip positioned on or near the distal end of the device and/or the portal. For example, in an embodiment, the expandable and/or contractible band and/or clip is removed from the distal end of the portal and/or the device and positioned on the atrial appendage so as to encircle at least a portion of the atrial appendage and thereby exclude the atrial appendage from the atrium to which the appendage is attached. In this embodiment, an inflatable member may be used to secure the expandable and/or contractible band and/or clip on the distal end of the portal and/or the device. For example, in an embodiment, the expandable and/or contractible band may be positioned proximal to the inflatable member, such deflating the inflatable member can release the expandable and/or contractible band and/or clip from the distal end of the portal and/or the device. Or, the expandable and/or contractible band or clip can be positioned substantially on top of the inflatable member, such that inflating the inflatable member urges the expandable and/or contractible band and/or clip from the distal end of the portal and/or the device.

In an embodiment, the expandable (and/or contractible) band and/or clip used in the methods of the invention is configured to close around the atrial appendage upon emplacement of the clip and/or band on the atrial appendage. In certain embodiments, the expandable and/or contractible band and/or clip is removed from the distal end of the portal and/or the device and positioned on the atrial appendage so as to encircle at least a portion of the atrial appendage to exclude the atrial appendage from the atrium to which the appendage is attached Additionally or alternatively, the distal end of the device and/or the portal may be configured to be collapsible around an atrial appendage. In some embodiments, the expandable and/or contractible band and/or clip is releasably secured to the inner lumen of the portal and/or the device. For example, a suture may be used to releasably secure the expandable and/or contractible band and/or clip to the inner lumen of the portal and/or the device such that cutting the suture will release the expandable and/or contractible band and/or clip from the distal end of the portal and/or the device.

In certain embodiments of the method, the clip and/or band may be shaped to have at least two longer sides and two shorter sides such that when the clip and/or band is closed around the atrial appendage, the longer sides flatten the appendage in a manner so as to substantially avoid plication of the appendage. For example, the clip or band may be oval, rectangular or diamond in shape. Or, clips and/or bands of other shapes may be used, such that when the clip and/or band is contracted, it can occlude the atrial appendage. In an embodiment, the distal end of the device and/or the portal is configured to be collapsible around an atrial appendage.

In some embodiments, the distal end of the portal and/or device is shaped to collapse around an atrial appendage without the application of force. In such embodiments, the portal and/or the device may comprise a mechanism to open the distal end. For example, the mechanism to open the distal end of the portal and/or the device may comprise at least one bar that when urged distally, pushes the distal end of the portal and/or the device from a naturally closed configuration to an open configuration. In an embodiment, the clip and/or band is releasably engaged with the distal end of the portal and/or the device, such that when the clip and/or band is collapsed around an atrial appendage, the clip or band may be released from the end of the portal and/or the device so as to collapse around at least a portion of the atrial appendage.

For example, in an embodiment, the portal and/or the device comprises a collapsible distal end with a clip and/or band that can be positioned in the distal end of the portal and/or the device and then allowed to collapse around an atrial appendage and comprising the steps of: using suction to positioning the atrial appendage in the distal end of the portal and/or the device; collapsing the distal end of the portal and/or the device and associated clip and/or band around the atrial appendage; and releasing the clip and/or band from the AA portal and/or the device so that the clip and/or band remains on the atrial appendage when the portal is removed.

The present invention also comprises systems for occluding or removing an atrial appendage. For example, the system may comprise a device for tying off an atrial appendage, and an AA portal and/or a pericardial portal. In certain embodiments the system may comprise a device for performing a surgical procedure on an atrial appendage via a pericardial approach, wherein at least a portion of the device is configured for insertion of at least a portion of the atrial appendage into a portion of the device and configured to exclude and/or remove an atrial appendage from an atrium to which the appendage is attached and a portal for positioning the device in close proximity to the atrial appendage.

In certain embodiments for the systems of the invention, at least a portion of the distal end of the AA portal and/or the pericardial portal is curvilinear such that the distal opening is not parallel to the proximal opening and the longitudinal axis of the lumen is not linear. In this way, the portal may comprise a configuration suitable to abut the atrial surface, while being manipulated via a subxypoid entry.

Also, in certain embodiments of the systems, the AA portal is configured to be inserted into an outer pericardial portal, where the pericardial portal comprises a proximal end having an opening and a distal end having an opening and a lumen connecting the proximal and distal openings. In this way, the outer pericardial portal may be used to deliver the AA portal to the site of the atrial appendage. Also, in certain embodiments, the AA portal and/or the pericardial portal may further comprise an inner cannula within the lumen of the portal, the inner cannula comprising a proximal end having an opening and a distal end having an opening and a lumen connecting the proximal and distal openings. For example, the inner cannula may be used to deliver surgical tools and other devices to the site of the atrial appendage. Also, in certain embodiments, either the AA portal or the outer percardioscopic portal may comprise an endoscope within at least a portion of the lumen of the portal.

The atrial and/or pericardial portal may be designed so that the distal end can be securely positioned on or near the atrial surface to allow for surgical procedures to be performed. For example, in certain embodiments suction can be applied within the lumen of the AA portal to create a seal between the distal opening of the AA portal and at least part of the atrial appendage. Also, in certain embodiments, the AA portal and/or the pericardial portal and/or the device for use with the pericardial portal may comprise a soft material surrounding the distal opening. In an embodiment, the soft material provide a cushion to reduce trauma to the atrial surface and/or to increase sealing between the distal end of the AA portal and the atrial surface.

The following non-limiting embodiments may apply to each of the devices, systems and methods of the invention.

In various embodiments of the devices, systems and methods of the present invention, the AA portal may comprise a device that is separate from the AA portal to exclude and/or remove an atrial appendage from an atrium to which the appendage is attached. A variety of devices suitable for occluding and/or isolated an atrial appendage from the atrium may be used.

For example, in one embodiment, the device comprises a tying band configured to be tied around a portion of the atrial appendage. In an embodiment, the tying band is a suture. In an embodiment, at least a portion of the suture comprises a material designed to cushion the suture.

In another embodiment, the device may comprise an expandable and/or contractible band. The band may be positioned on or near the distal end of the AA portal. Or, the band may be positioned on the distal end of a device that is delivered to the atrial appendage via a pericardial portal.

In certain embodiments, the AA portal, pericardial portal, or the device used with a pericardial portal may further comprise an inflatable member positioned on the distal end of the portal and/or the device. Also, the portal (i.e., AA or pericardial) and/or device may further comprise a lumen configured to inflate the inflatable member. In this way, an expandable and/or contractible band may be positioned proximal to the inflatable member such that when the inflatable member is inflated, the band is secured on the distal end of the portal and/or the device, and when the inflatable member is deflated, the band can be urged over the deflated inflatable member and released from the distal end of the portal and/or the device.

For example, an outer cylinder concentric with the outer diameter of the device used with a pericardial portal and/or an AA portal may be positioned near the distal end of the AA portal or the device. In an embodiment, the outer cylinder has an inner diameter that is larger than the outer diameter of the AA portal or device, but smaller than the outer diameter of the expandable and/or contractible bands. In this way, when the outer cylinder is advanced distally, it can urge the band off of the AA portal or the device and onto the atrial appendage.

In one embodiment, the device for occluding an atrial appendage may comprise a distal end having an opening and a lumen, wherein the distal end is configured for insertion of at least a portion of the atrial appendage into the distal opening. The device may further comprise an element (e.g., pincers or another type of grabbing element) that is used to pull the atrial appendage into the lumen of the device. Or, suction may be used to pull the atrial appendage into the device. Then, an expandable and/or contractible band positioned on the distal end of the device may be removed from the distal end of the device and positioned on the atrial appendage to occlude the atrial appendage. For example, an outer cylinder concentric with the outer diameter of the device may be positioned near the distal end of the device. In an embodiment, the outer cylinder has an inner diameter that is larger than the outer diameter of the device, but smaller than the outer diameter of the expandable and/or contractible bands. In this way, when the outer cylinder is advanced distally, it can urge the band off of the device and onto the atrial appendage.

Or, the expandable and/or contractible band positioned on the distal end of the AA portal and/or the device used with a pericardial portal may be positioned substantially on top of an inflatable member, such that when the inflatable member is deflated, the band is secured on the distal end of the portal, and when the inflatable member is inflated, the band is pushed off of the distal end of the portal or the device.

In certain embodiments, the distal end of the AA portal or the device used with a pericardial portal is sufficiently flexible so as to be collapsed around the end of an atrial appendage. Or, the distal end of the AA portal or the device used with a pericardial portal may be substantially firm, so as to maintain an open configuration throughout the procedure.

Also, in certain embodiments, the AA portal or the device used with a pericardial portal may further comprise a clip and/or band positioned at the distal end of the portal or the device which may be positioned around an atrial appendage so as to occlude the atrial appendage from the remainder of the atrium. In certain embodiments, the clip and/or band is shaped to have at least two longer sides and two shorter sides such that when the clip and/or band is closed around the atrial appendage, the longer sides flatten the appendage in a manner so as to substantially avoid plication of the appendage. For example, in alternate embodiments, the clip or band is oval, rectangular or diamond in shape.

In certain embodiments, the distal end of the AA portal or the device used with a pericardial portal is shaped to collapse around an atrial appendage without the application of force. In these embodiments, the AA portal or the device used with a pericardial portal may comprise a mechanism to open the distal end of the portal and/or the device. For example, and as discussed in detail below, the mechanism to open the distal end of the portal or the device used with a pericardial portal may comprise at least one bar or other type of mechanism to apply force that when urged distally, can push the distal end of the portal and/or the device from a naturally closed configuration to an open configuration.

In certain embodiments, the clip and/or band is releasably engaged with the distal end of the portal or the device used with a pericardial portal, such that when the clip and/or band is collapsed around an atrial appendage, the clip or band may be released from the end of the portal or the device so as to collapse around at least a portion of the atrial appendage.

For example, in certain embodiments, the present invention comprises a device for tying off a left atrial appendage (LAA) or right atrial appendage (RAA), wherein the device comprises a cushioned suture material that may be used to tie off an atrial appendage. In an embodiment, an endoscopic loop of braded, non-absorbable suture (Ethicon, Autosuture) modified to include a strip of felt pledget to prevent injury to the base of the AA may be used. The device may comprise a component for tightening the cushioned suture around the appendage. For example, in one embodiment, a pair of sturdy knot pushers arranged on either side of the cushioned suture may be used. In other embodiments, and as described in more detail below, an elastic type of band may be used to tie off the atrial appendage or exclude the atrial appendage from circulation. In other embodiments, and as described in more detail below, a clip device may be used to tie off the atrial appendage or exclude the atrial appendage from circulation. In other embodiments, and as described in more detail below, an elastic type of clip device may be used to tie off the atrial appendage or exclude the atrial appendage from circulation.

In each of the devices, systems and methods of the invention, the AA portal or the device used with a pericardial portal may be configured specifically to access either the left atrial appendage or the right atrial appendage.

For example, in certain embodiments, the methods of the invention may comprise inserting an atrial appendage portal of the invention, or a device of the invention into an outer pericardial portal and positioning the distal opening of the atrial appendage portal or the device at the surface of the atrium. In an embodiment, at least a portion of the distal end of the atrial appendage portal, pericardial portal, or the device is curvilinear such that the distal opening is not parallel to the longitudinal axis. Also, an endoscope may be used to provide an image of body structures present near the distal end of the portal or the device. The method may further comprise applying suction within the lumen of the atrial appendage portal or the device used with a pericardial portal to create a seal between the distal opening of the portal and/or the device and at least part of the atrial appendage.

The method may, in certain embodiments, comprise positioning one of the devices described herein to exclude and/or remove an atrial appendage at the distal end of the atrial appendage portal.

For example, in one embodiment, the AA portal or the device to be used with a pericardial portal comprises a tying band configured to be tied around a portion of the atrial appendage. In an embodiment, the tying band is a suture. Or other types of tying elements, e.g., string, thread, plastic or metal wires, and the like may be used. In an embodiment, at least a portion of the suture comprises a material designed to cushion the suture. In this embodiment, the method may comprise providing the suture at the distal opening of an AA portal or the device used with a pericardial portal, using the suture to encircle at least a portion of the atrial appendage, and tightening the suture around the atrial appendage to exclude the atrial appendage from the atrium to which the appendage is attached.

In certain embodiments, the distal end of the atrial appendage portal or the device used with a pericardial portal may be configured to be collapsible around an atrial appendage. Or, the distal end of the atrial appendage portal or the device used with a pericardial portal may be substantially firm, so as to maintain an open configuration throughout the procedure.

In other embodiments, and as described in detail herein, the device for tying off or occluding the atrial appendage may comprise an expandable and/or contractible band and/or clip positioned on or near the distal end of the AA portal or the device used with a pericardial portal. Thus, in certain embodiments of the methods of the invention the expandable and/or contractible band is removed from the distal end of the portal or the device used with a pericardial portal so as to encircle at least a portion of the atrial appendage to exclude the atrial appendage from the atrium to which the appendage is attached. In an embodiment, and as described in more detail below, the expandable and/or contractible band or clip is configured to close around the atrial appendage upon emplacement of the clip and/or band on the atrial appendage.

In certain embodiments, an expandable and/or contractible band or clip for occluding or tying off the atrial appendage may be releasably secured to the inner lumen of the atrial appendage portal or the device used with a pericardial portal. In certain embodiments, the expandable and/or contractible band or clip may comprise a suture to secure the expandable and/or contractible band or clip to the inner lumen of the atrial appendage portal or the device used with a pericardial portal.

In certain embodiments, the clip and/or band is shaped to have at least two longer sides and two shorter sides such that when the clip and/or band is closed around the atrial appendage, the longer sides flatten the appendage in a manner so as to substantially avoid plication of the appendage. For example, in alternate embodiments, the clip or band is oval, rectangular or diamond in shape.

In certain embodiments, the distal end of the AA portal or the device used with a pericardial portal is shaped to collapse around an atrial appendage without the application of force. In these embodiments, the AA portal or the device used with a pericardial portal may comprise a mechanism to open the distal end of the AA portal and/or the device. For example, and as discussed in detail below, the mechanism to open the distal end of the AA portal and/or the device may comprise at least one bar or other mechanism that can be used to apply force that when urged distally, pushes the distal end of the AA portal and/or the device from a naturally closed configuration to an open configuration.

In certain embodiments, the clip and/or band is releasably engaged with the distal end of the AA portal or the device used with a pericardial portal, such that when the clip and/or band is collapsed around an atrial appendage, the clip or band may be released from the end of the AA portal or the device so as to collapse around at least a portion of the atrial appendage.

Or, the method may comprise using an inflatable member positioned on the distal end of the AA portal or the device used with a pericardial portal to secure the band or clip on the distal end of the portal. For example, in an embodiment, an expandable and/or contractible band is positioned proximal to the inflatable member such that when the inflatable member is inflated, the band or clip is secured on the distal end of the portal or the device used with a pericardial portal, and when the inflatable member is deflated, the band or clip can be released from the distal end of the portal or the device used with a pericardial portal. Alternatively, the expandable and/or contractible band or clip may be positioned substantially on top of the inflatable member, such that when the inflatable member is deflated, the band or clip is secured on the distal end of the portal or the device used with a pericardial portal, and when the inflatable member is inflated, the band or clip is pushed off of the distal end of the portal or the device used with a pericardial portal.

In other embodiments, the present invention comprises systems for tying off an atrial appendage. For example, the system may comprise a device for tying off an atrial appendage, and an AA portal and/or a pericardial portal. In certain embodiments, the device used with the system comprises a suture configured to be tied around a portion of the atrial appendage. Also, in certain embodiments, at least a portion of the suture comprises a material designed to cushion the suture. Or, in other embodiments, and as described in more detail below, an elastic type of band may be used to tie off the atrial appendage or exclude the atrial appendage from circulation. Or, in other embodiments, and as described in more detail below, a clip may be used to tie off the atrial appendage or exclude the atrial appendage from circulation. Or, in other embodiments, and as described in more detail below, an elastic type of band or clip may be used to tie off the atrial appendage or exclude the atrial appendage from circulation.

As described in more detail herein, the AA portal may comprise a single portal and/or may be used in conjunction with a second, outer cannula or portal. In certain embodiments, the system comprises an outer pericardial portal for delivering the AA portal and/or the device for occluding the atrial appendage to an atrial appendage.

The AA portal or the device used with a pericardial portal may use an expandable/contractible band and/or a clip for tying off the atrial appendage. The band and/or clip may be positioned on the outer circumference or the inner circumference of the distal end of the AA portal or the device used with a pericardial portal. In certain embodiments, the band/clip for occluding the AA may be releasably attached (e.g., via a suture that can be cut) at the distal end of the AA portal or the device. Or, in certain embodiments, the AA portal or the device may be configured such that a band and/or clip for occluding the atrial appendage (e.g., an atrial tying band/clip) may be positioned by urging the band/clip through the inner lumen to the distal end of the AA portal and/or the pericardial portal.

The expandable/contractible band and/or clip may be, in certain embodiments, an elastic (or other expandable) circular band as described in more detail herein. The band/clip may be, in certain embodiments, a rectangular, square, circular or oval clip as described in more detail herein.

Thus, in certain embodiments, upon insertion of the atrial appendage into the AA portal or the device used with a pericardial portal, a band and/or clip positioned on the outer circumference of the AA portal or the device can then be slipped off of the end of the AA portal or the device and onto the atrial appendage (e.g., at or near the base of the atrial appendage) so as to constrict the atrial appendage in a way such that most or all of the atrial appendage is functionally isolated from the rest of the heart. For example, an outer cylinder concentric with the outer diameter of the device may be positioned near the distal end of the device. In an embodiment, the outer cylinder has an inner diameter that is larger than the outer diameter of the device and/or the atrial appendage portal, but smaller than the outer diameter of the expandable and/or contractible bands. In this way, when the outer cylinder is advanced distally, it can urge the band off of the device and/or the atrial appendage portal and onto the atrial appendage.

In other embodiments, upon insertion of the atrial appendage into the AA portal, a tying band positioned on the inner circumference of the AA portal or the device can be slipped off of the end of the AA portal or the device and onto the atrial appendage (e.g., at or near the base of the atrial appendage) so as to constrict the atrial appendage in a way such that most or all of the atrial appendage is functionally isolated from the rest of the heart. In certain embodiments, upon insertion of the atrial appendage into the AA portal or the device, the band and/or clip may be urged through the inner lumen of the AA portal or the device and slipped onto the atrial appendage (e.g., at or near the base of the atrial appendage) so as to constrict the atrial appendage in a way such that most or all of the atrial appendage is functionally isolated from the rest of the heart.

Also, in certain embodiments, the AA portal, the pericardial portal, or the device used with a pericardial portal may have an inflatable member positioned at the distal end. The inflatable member (e.g., balloon) may in certain embodiments, minimize any trauma that can result from contact of the portal(s) and/or the device with the atrial appendage (e.g., as the atrial appendage is engaged by the AA portal).

Additionally and/or alternatively, the inflatable member (e.g., balloon), or a second inflatable member, may in certain embodiments, help keep an expandable and/or contractible band and/or clip on the AA portal or the device used with a pericardial portal until the band and/or clip is ready to be positioned on the atrial appendage. For example, once the atrial appendage is inserted into the AA portal or the device, the balloon may be deflated such that the band and/or clip can be slipped off of the distal end of the AA portal or the device and onto the atrial appendage. For example, in an embodiment, the expandable and/or contractible band and/or clip is positioned proximal to the inflatable member such that when the inflatable member is inflated, the band and/or clip is secured on the distal end of the portal and/or device, and when the inflatable member is deflated, the band can be released from the distal end of the portal and/or device.

Additionally and/or alternatively, an inflatable member (e.g., balloon) may in certain embodiments, be used to push the expandable and/or contractible band and/or clip off of the end of the AA portal or the device used with a pericardial portal and on to the atrial appendage. For example, in an embodiment, the expandable and/or contractible band is positioned substantially on top of the inflatable member, such that when the inflatable member is deflated, the band is secured on the distal end of the portal or the device, and when the inflatable member is inflated, the band is pushed off of the distal end of the portal or the device.

Additionally and/or alternatively, other control release mechanisms (e.g., balloon, lever, sutures) may be used to position the expandable and/or contractible band and/or clip off of the end of the AA portal or the device used with a pericardial portal and on to the atrial appendage. For example, in an embodiment, the expandable and/or contractible band and/or clip is positioned within the inner lumen of the AA portal or the device used with a pericardial portal such that when the band and/or clip is open, it is secured on the distal end of the portal or the device used with a pericardial portal and when released, the band and/or clip closes around the atrial appendage and is released from the distal end of the AA portal or the device used with a pericardial portal. In certain embodiments, the band/clip for tying off the AA may be releasably attached (e.g., via a suture that can be cut) at the distal end of the AA portal or the device used with a pericardial portal for release and positioning on an AA.

Additionally and/or alternatively, the expandable and/or contractible band and/or clip may be positioned by urging the band and/or clip through the lumen of the AA portal or the device and on to the atrial appendage. For example, in an embodiment, the expandable and/or contractible band and/or clip is positioned on a separate device and urged through the inner lumen of the AA portal, pericardial portal, or a device used with a pericardial portal, such that when the AA portal or the pericardial portal is open, the band and/or clip is secured on the distal end of the portal or the device, and when released, the band and/or clip closes around the atrial appendage.

The present invention also comprises methods for using a pericardial or subxyphoid approach to provide atrial appendage therapies. The method may comprise the steps of inserting a device for tying off an atrial appendage (e.g., knot pushers and suture, or an expandable and/or contractible band and/or clip) into an AA portal or a pericardial portal, or inserting an AA portal having such a device positioned at its distal end into a pericardial portal.

In certain embodiments, the AA portal or pericardial portal is a subxyphoid cannula. Or, the AA portal may be used in conjunction with an outer pericardial portal. The method may then comprise using the pericardial portal or AA portal to access the pericardial sac as described herein. The pericardial portal or AA portal may then be maneuvered within the pericardial sac until the distal end of the pericardial portal or AA portal abuts the atrial appendage.

Thus, in certain embodiments, a single portal may be used. In other embodiments, the AA portal may be used with an outer pericardial portal having a lumen into which the AA portal is inserted. Or in other embodiments, a pericardial portal is used in combination with the device for occluding the atrial appendage.

For example, where an inner AA portal or a device used with a pericardial portal is used, the AA portal or the device used with a pericardial portal may be manipulated through an outer percardioscopic portal such that the distal end of the AA portal or the device used with a pericardial portal abuts the tip of the atrial appendage. Once the tip of the atrial appendage is adjacent to the distal end of the AA portal or the device used with a pericardial portal, suction may be applied to the AA portal or the device to aspirate at least a portion of the atrial appendage into the AA portal or the device.

At this point, in certain embodiments, the expandable and/or contractible band and/or clip may be released at the distal end of the AA portal or the device used with a pericardial portal and onto the atrial appendage. The band and/or clip can then contract around the atrial appendage so as to be snugly positioned on the atrial appendage and tie off the atrial appendage from the rest of the atrium.

In other embodiments, a cushioned suture may be manipulated through a AA portal or the pericardial portal so as to abut or almost abut the atrial appendage. Next, the cushioned suture may be positioned around the atrial appendage manually by the operator (e.g., physician), and then tightened around the atrial appendage so as to tie off the atrial appendage from the rest of the atrium.

The AA portal and/or pericardial portal may, in certain embodiments, comprise an endoscope to allow the user to visualize the distal end of the portal.

Also, in various embodiments, the AA portal and/or the pericardial portal and/or the device used with a pericardial portal may have a curvilinear distal portion such that the distal opening is not parallel to the proximal opening of the delivery cannula.

In some embodiments, either the percardioscopic portal or the AA portal may comprise an inner access member (e.g., an inner cannula), wherein the inner cannula is configured to be inserted in the percardioscopic portal and/or the AA portal. Or, multiple inner access members may be used.

Additionally, in certain embodiments, suction can be applied within the lumen of the percardioscopic portal and/or the AA portal and/or the device used with a pericardial portal. Also, in certain embodiments, the pericardial portal and/or the AA portal and/or the device used with a pericardial portal may comprise a soft material surrounding the distal opening such that when the portal or the device used with a pericardial portal is positioned to have the distal opening abut atrial appendage, and as suction is applied within the lumen of the portal, a seal is formed between the distal opening of the portal and the atrial appendage. Additional embodiments of the portals as described herein may be employed with the devices, systems and methods for atrial therapy.

The present invention may be understood by reference to the figures and following description of example embodiments of the invention.

FIG. 1 demonstrates the insertion of an AA portal (2) or a pericardial portal in the subxyphoid position in accordance with an embodiment of the present invention. In an embodiment, an incision (4) is made in the midline of the epigastrium just below the xyphoid process. The incision can be extended through the subcutaneous fat and the midline fascia but remains outside the peritoneal cavity. The incision can then be continued further cephalad until the pericardium is encountered. The pericardium may then be entered sharply and a defect created large enough to easily accept the portal. The portal can then be positioned behind the sternum within the pericardium and directed to the LAA (6) or the RAA on the heart (8). Visualization can be provided by an endoscope (10) inside the inner lumen of the portal.

Figure 2:
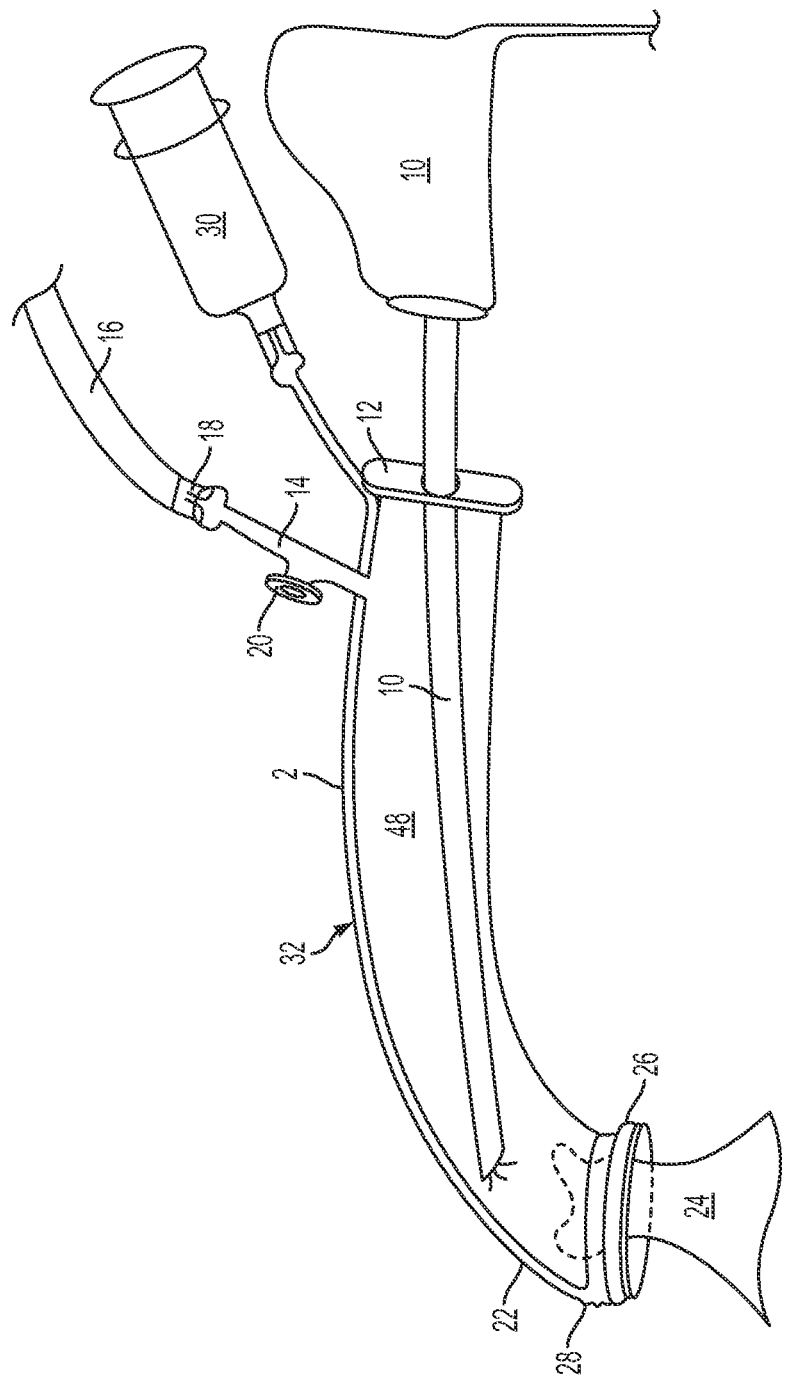
FIG. 2 illustrates an AA portal and associated endoscope in accordance with an embodiment of the present invention, showing the LAA within the distal opening of the AA portal and visualized with the endoscope.

FIG. 2 demonstrates an AA portal of the invention (2) and endoscope (10) in the inner lumen (48) of the AA portal, where the distal end of the AA portal is abutting an atrial appendage (e.g., LAA) (24). In an embodiment, a cap (12) on the proximal end of the AA portal, allows the endoscope access into the lumen (48) and provides an air tight seal to contain suction within the lumen (48).

In one embodiment as depicted here, the central lumen (48) of an AA portal is continuous with a side port (14) which may be connected to suction (16) via a connector (18). In one embodiment, an opening (20) for the side port (14) is connected to the central lumen (48) of the AA portal. In this way, when suction is applied to the side port (14), application of suction to the distal end (22) of the AA portal at the LAA (24) may be controlled by occlusion of the opening (20). For example, when the opening (20) is covered, the vacuum provided (16) is applied to the distal end (22). As discussed in more detail herein, a similar configuration may be used to provide suction in the inner lumen of a device used with the pericardial portal.

Also shown in FIG. 2 is an expandable AA (e.g., occlusion) band (26) located on the outer circumference of the distal end of the AA portal (2) and overlying an inflatable member (e.g., balloon) (28). In an embodiment, the balloon (28) may be inflated and deflated via a plunger syringe (30) (or a similar type device that can be used to inflate a balloon) which passes air or fluid into the balloon (28) via a lumen (32) separate from the central lumen of the AA portal. As noted herein, in certain embodiments, deflation of the balloon allows for the expandable and/or contractible band (26) to contract such that the band is not tightly fixed on the end of the AA portal, and can be slipped off onto the base of the LAA (24) or the RAA. For example, in some embodiments, an outer cylinder may be urged distally along the length of the AA portal and used to engage the band so as to push the band distally off the end of the AA portal.

FIG. 3 illustrates the distal end of an AA Portal (2) and occlusion/exclusion of an AA (24) using an AA portal knot pusher (34) and a felt reinforced lasso-type tying band (36). Or, such a an AA portal knot pusher (34) and a felt reinforced lasso-type tying band (36) can be delivered to the atrial appendage using a pericardial portal. Or, such an AA portal knot pusher (34) and a felt reinforced lasso-type tying band (36) can be delivered to the atrial appendage using an AA portal inserted into a pericardial portal.

An endoscope (10) within the lumen of the AA portal may provide visualization of the LAA (24) within the central lumen (48) of the AA portal (and/or a pericardial portal). In one embodiment, suction may be applied to the central lumen (48) of the AA portal (2) which encourages the LAA (24) into the central lumen (48) and into the felt reinforced lasso (36) (FIG. 3A). In certain embodiments, the application of suction can be used to create a seal between the epicardium surrounding the LAA (38) and the distal end of the AA portal (2). Once the LAA (24) is adequately within the tying band (36), the operator may, using an accessory device such as a cannula or other device that can access the distal end of the lasso, manipulate the AA portal knot pusher (34) to cinch the tying band around the base of the LAA in the proper location.

FIG. 3B demonstrates the tying band (36) tight around the base of the LAA (24) after the vacuum has been released and the AA portal (2) has been withdrawn from the epicardium (38). The tying band (36) may be held secure by the knot (40) created by the suture (42) that was within the knot pusher. Once security is verified, the remaining suture can be divided and removed.

FIG. 4 further demonstrates one embodiment of the use of a lasso-type tying band for tying off an atrial appendage using a pericardial approach with an AA portal or a pericardial portal. FIG. 4A shows the distal end of a tying band comprising an endoscopic loop/loops of suture (42) reinforced with felt as a cushion (44). Or, other types of material to cushion and reinforce the suture may be used. More than one knot pusher (34) and more than one loop of suture (42) may be used.

Figure 4A:
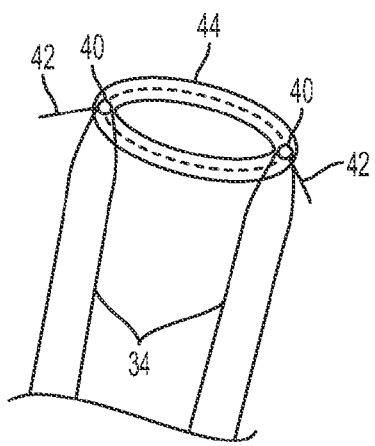
FIG. 4, panels A-C, illustrates the use of a device for tying off an AA (e.g., LAA) using a pericardial approach in accordance with an embodiment of the present invention, where panel A shows a top view of the felt-covered suture and two knot pushers, panel B shows the felt and suture emplaced on the AA, panel C shows the process of the two knot pushers tightening the suture on the AA, panel D shows the suture tightened on the AA and panel E shows a perspective view of the felt covered suture and two knot pushers within the AA portal.
Figure 4B:
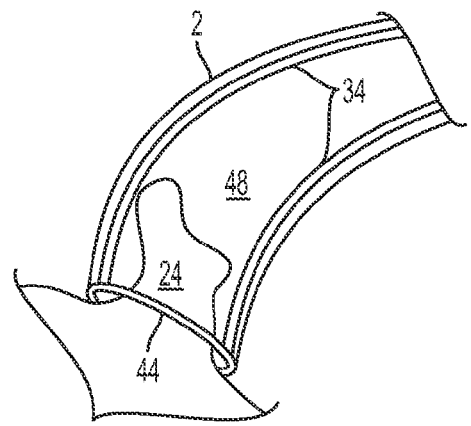
Figure 4C:
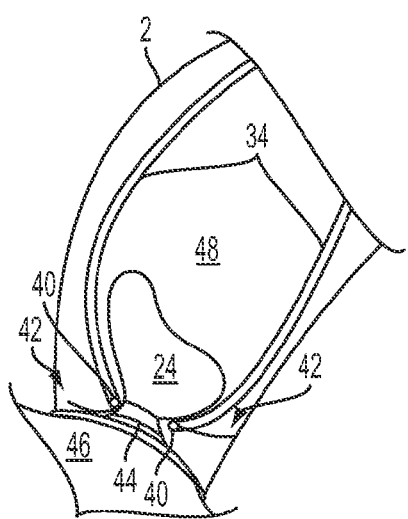
Figure 4D:
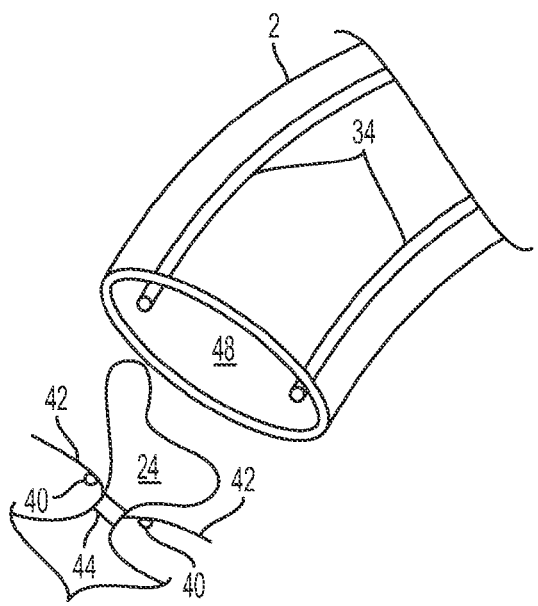
Figure 4E:
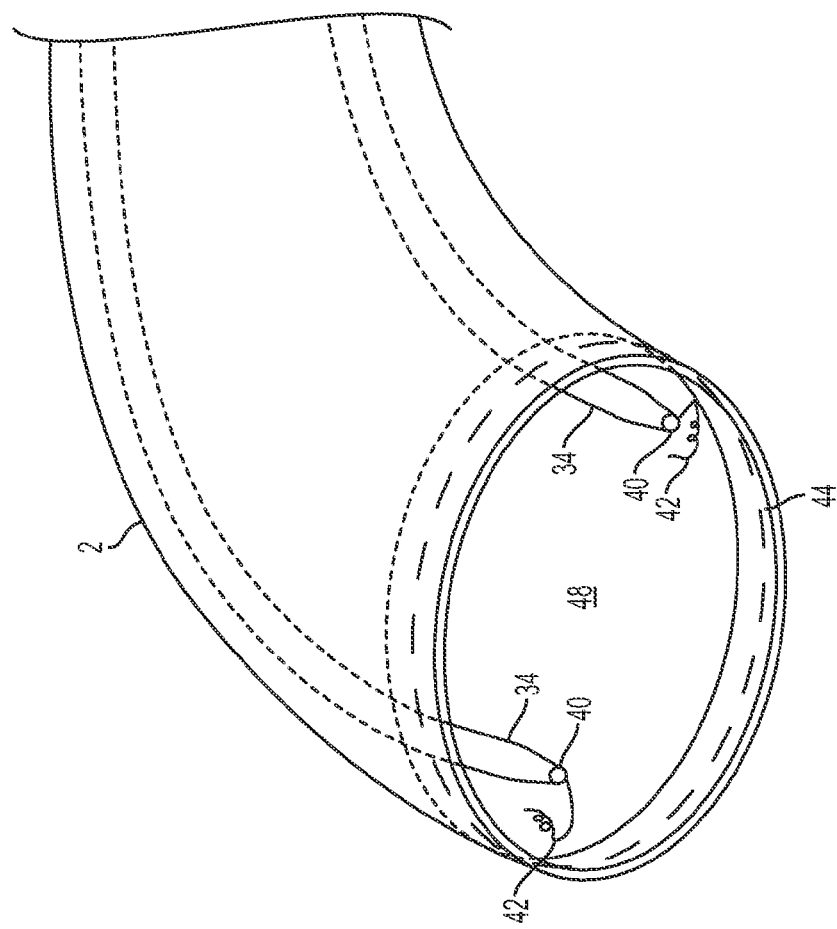
Figure 5A:
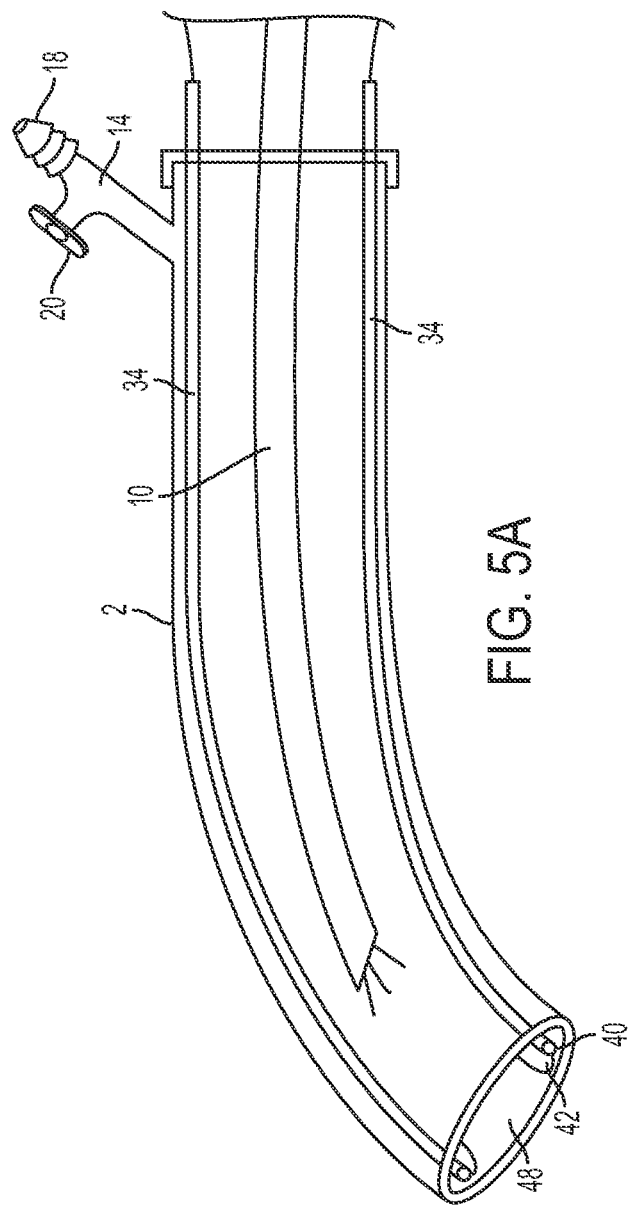
FIG. 5, panels A-D, illustrates a method of deploying a device for isolation of an AA according an alternate embodiment of the present invention, where panel A shows an AA portal having an atrial tying band on its distal end with two knot pullers and an endoscope disposed within the lumen of the AA portal, panel B shows the AA portal positioned next to the LAA, panel C shows the LAA aspirated into the AA portal, and panel D shows the band having been removed from the AA portal and positioned on the LAA.
Figure 5B:
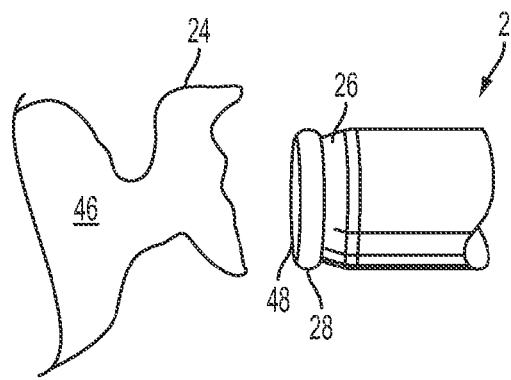
Figure 5C:
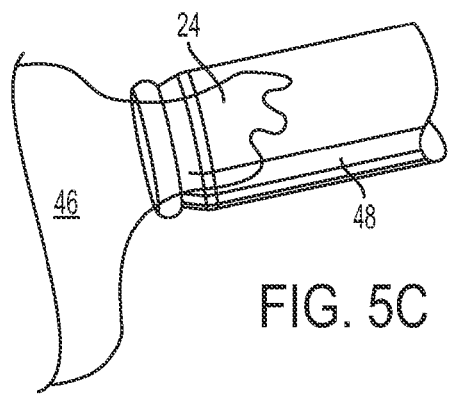
Figure 5D:
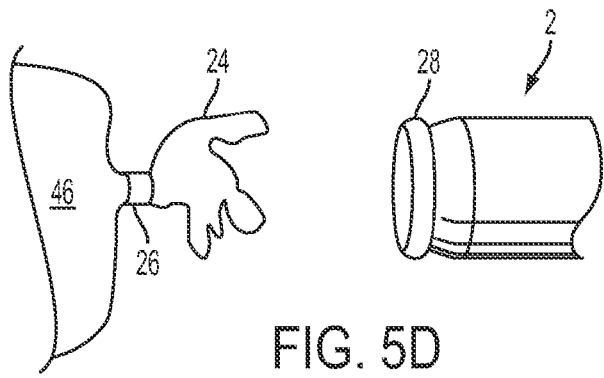

For example, in one embodiment, a braided suture (42) is threaded through an appropriately sized piece of cushioning material and tied in an adjustable manner (e.g., a slip knot or other adjustable loop) (40). In alternate embodiments, the felt may have a diameter of about 1 to 10 mm, or 2 to 8 mm, or 3 to 7 mm, or 4 to 6 mm, or about 5 mm. Also, in alternate embodiments, the cushioning material may have a length of about 1 to 10 cm, or 2 to 8 cm, or 3 to 7 cm, or 4 to 6 cm, or about 5 cm. The cushioning material may be placed around the LAA (24) (FIG. 4B) using a sturdy knot pusher or more than one knot pusher (34) (FIG. 4B). The knot pusher(s) (34) may be used to tighten the knot (40) around the base of the LAA (24) until it is secure and excludes the LAA (24) from the left atrium (46) (FIG. 4C). Once secured (FIG. 4D), the suture (42) may be cut using a cutting tool that can also be delivered to the site using the atrial appendage portal of the present invention. The LAA can then be safely excised using an endoscopic stapling device such as those that are commercially available (Ethicon, Covidian). This improved device as well as the AA endoscopic loop can be positioned under direct endoscopic visualization using the endoscope within the paracardioscopic cannula. The felt cushion (44) and loop of the suture (42) with adjustable knot (40), in one embodiment, may be mounted inside the opening of the distal lumen (48) (FIG. 4E) so that when the knot pusher/pushers (34) are advanced, the cushion (44) and suture loop (42) are released from the cannula (2) and secured around the base of the LAA (24).

FIG. 5 further illustrates an embodiment of using a AA portal having an expandable/contractible band at its distal end along with an endoscope present within the lumen. In this embodiment, a cylindrical AA Portal (2) (FIG. 5A) may be delivered to the LAA alone (FIG. 5B) or via an outer paracardioscopic cannula/portal, and used to aspirate the LAA into a central lumen (48) (FIG. 5C). The end of the AA portal (2) may, in certain embodiments, be covered by an inflatable balloon (28) so as to be less traumatic to the LAA. An elastic band (26) can be loaded over this balloon, or may be positioned on the outer circumference of the AA portal, but proximal to the balloon. In this way, the balloon when inflated will keep the band on the end of the device.

FIG. 5 panels B-C, illustrates a method of deploying an expandable and/or contractible band for isolation of the LAA according to one embodiment of the present invention. As shown in FIG. 5B, the device may comprise a balloon (28) positioned on the distal end of the AA Portal (2). By inflating the balloon, a band (26) that is to be used to isolate the AA can be secured to the end of the delivery device (e.g., wherein the band is positioned on the outside circumference of the LAA, but proximal to the balloon). The central suction lumen (48) of the instrument may be positioned around the LAA (24) and suction applied to aspirate the LAA into the central lumen (FIG. 5C). Once the LAA (24) is within the AA portal (2), the balloon (28) at the distal end of the AA portal may be deflated to allow the AA band (26) to be released and positioned on the LAA 24 (FIG. 5D). This type of delivery mechanism may also be used with a device that is used in conjunction with a pericardial portal.

Figure 6A:
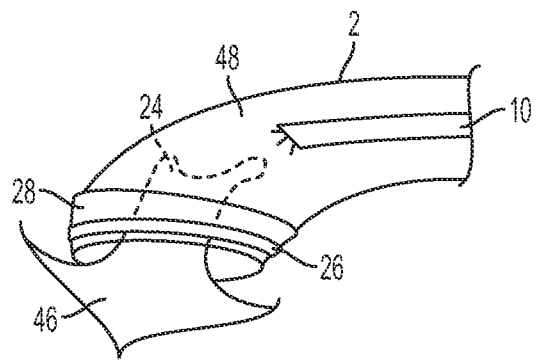
FIG. 6, panels A-B, illustrates a method of deploying a device for LAA (or RAA) exclusion and isolation in accordance with an embodiment of the present invention where panel A shows a curvilinear AA portal having a tying band on its outer circumference in approximation to the myocardium around the AA and the AA within the distal opening, and panel B shows the band removed from the distal end of the AA portal and emplaced around the base of the AA.
Figure 6B:
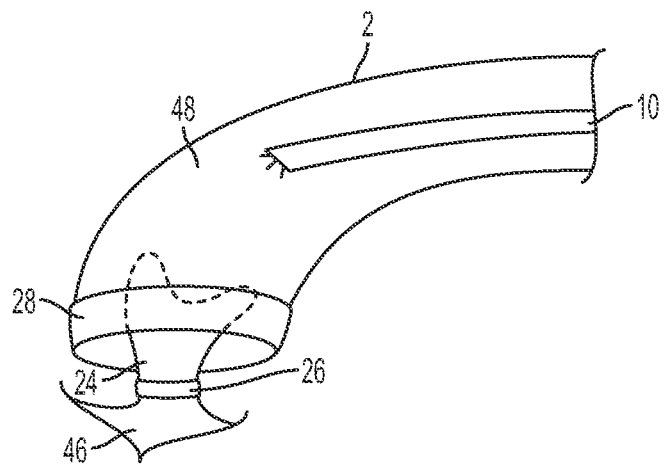

FIG. 6 demonstrates another embodiment showing the deployment of an expandable AA occlusion band (26) at the base of the LAA (24). In this embodiment, a balloon (28) at the distal end of an AA portal (2) may be inflated so as to push band (26) that is positioned on top of or distal to the balloon off of the distal end of the AA portal and onto the base of the LAA. Panel 6A shows the AA portal 2 positioned with the distal end of the portal around the LAA (24). In FIG. 6A, the balloon (28) is deflated and the band (26) is on the distal end of the AA portal (2). In FIG. 6B, the balloon (28) is inflated, thereby pushing the band (26) off of the distal end of the AA portal and onto the base of the LAA (24) where it can contract to occlude the AA. This type of delivery mechanism may also be used with a device that is used in conjunction with a pericardial portal.

In certain embodiments, the AA portal or the device that is used in conjunction with a pericardial portal may comprise a collapsible distal end with a clip and/or band that can be positioned in the distal end of the AA portal or the device that is used in conjunction with a pericardial portal and then allowed to collapse around an atrial appendage. In this embodiment, the AA portal or the device used with a pericardial portal may be positioned such that the atrial appendage is inserted into the distal end of the portal or the device, e.g., with the help of suction applied to the inner lumen of the AA portal or the device. Next, the distal end of the AA portal and associated clip and/or band may be collapsed around the atrial appendage. Once the clip and/or band is in position around the atrial appendage (so as to occlude the atrial appendage from the rest of the atrium), the clip and/or band may be released from the AA portal or the device so as to be left on the atrial appendage when the portal is removed.

Figure 7A:
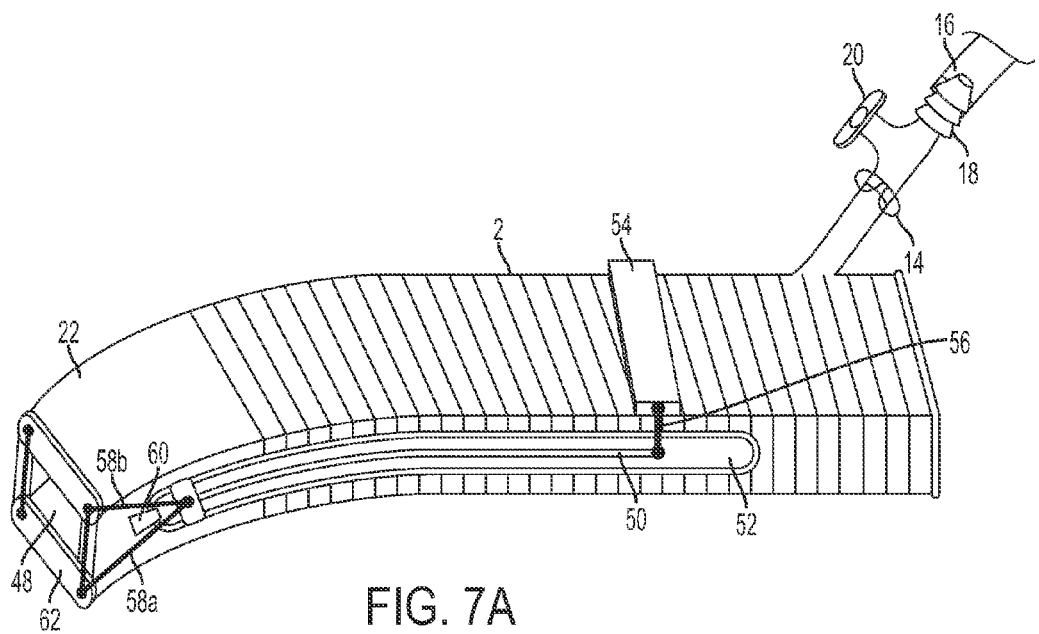
FIG. 7, panels A-C, illustrate a rectangular AA portal (panels A and B) or a device (panel C) used with a pericardial portal with an incorporated controllable release and deployment mechanism of the distal AA clip occlusion device in accordance with an embodiment of the present invention. Panels A and C illustrate the distal clip occlusion device in the open position; panel B illustrates the distal clip occlusion device in the closed position.

FIG. 7 demonstrates an embodiment of an AA portal or a device used with a pericardial portal having a collapsible distal end. This embodiment illustrates a rectangular portal with a mechanism for controlled release and deployment of a distal linear band/clip at the appendage. In one embodiment, the central lumen (48) of the AA portal is continuous with a side port (14) which may be connected to suction (16) via a connector (18). In one embodiment, an opening (20) for the side port (14) is connected to the central lumen (48) of the AA portal. In this way, when suction is applied to the side port (14), application of suction to the distal end of the AA portal (22) is controlled by occlusion of the opening (20). For example, when the opening (20) is covered, the vacuum is provided (16) to the distal end (22). The distal end of the portal (22) may be made of pliable and collapsible material (e.g., plastic, silicone and the like). In certain embodiments, the distal end of the portal may be held open by a sliding bar (50) or other similar type mechanism that can be used to apply force distally. In certain embodiments, the sliding bar may be contained within a slot (52) positioned on the side of the portal. In an embodiment, there are a plurality of slots. For example, in an embodiment, there is a slot (52) and a sliding bar (50) on two sides of the portal (back slot not visible in FIG. 7A). Both slots (52) may contain a sliding bar (50) which may be acted upon by moving a thumb bar (54) which is connected to the sliding bar (50) by a connecting bar (56). The distal end of the sliding bar (50) may divide into two (or more) separating bars (58a, 58b) which can be separated and forced apart by a fulcrum (60). When the thumb bar (54) is advanced distally, the sliding bar (50) may advance, pushing the separating bars (58a, 58b) against the fulcrum (60), thereby causing them to separate and open the distal linear band/clip and, therefore, the distal end of the portal (22). This action can hold the distal and pliable part of the portal (22) open. Or, other mechanisms for spreading (opening) the distal end of the portal may be used. In an embodiment, the atrial appendage may then be inserted into the open distal end of the AA portal.

Figure 7B:
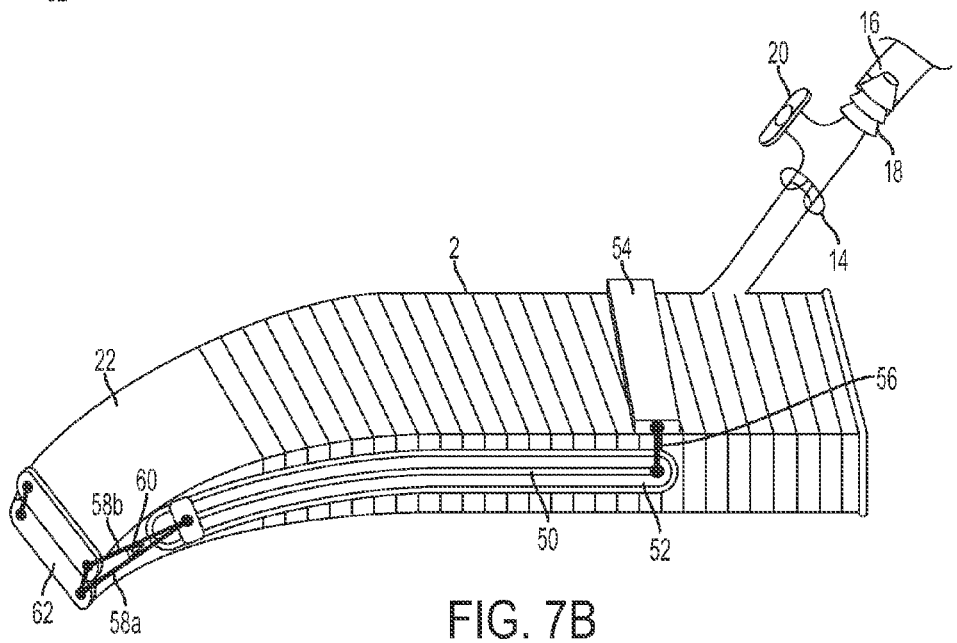

FIG. 7B illustrates a rectangular portal (2) with the distal end in the closed position. In this embodiment, the thumb bar (54) has been withdrawn proximally, retracting the sliding bar (50) and allowing the separating bars (58a, 58b) to come together and close the distal end of the portal (22). Also shown in FIGS. 7A and 7B is a linear clip/band (62) located at the distal end of the AA portal (2). In one embodiment, the linear band/clip may be designed with intrinsic elastic properties which act to force the linear band/clip closed. As described above, moving the thumb bar (54) distally or proximally, respectively, can open and close the linear band/clip (62). The linear band/clip (62), when in position, can be deployed and left in position at the appendage as the portal (2) is removed.

Figure 7C:
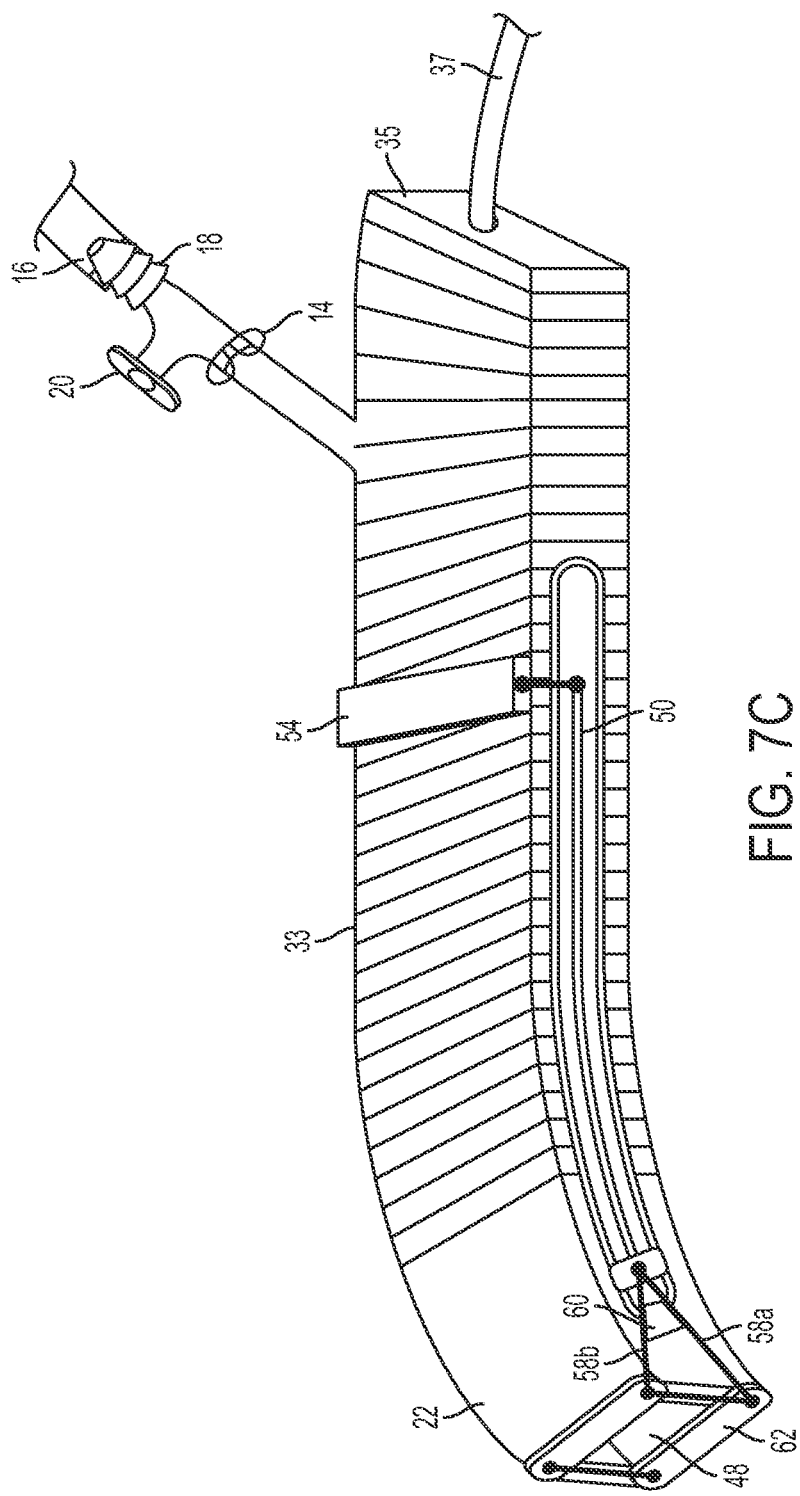
Figure 8A:
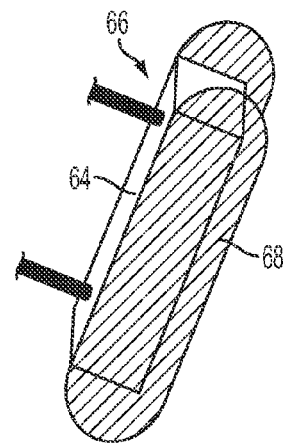
FIG. 8, panels A-E, illustrate a rectangular distal band/clip to be positioned at the distal end of the AA portal or a device used with a pericardial portal for occlusion of the appendage in accordance with an embodiment of the present invention. Panel A illustrates a view of a single side of the band/clip device; panel B illustrates the band/clip from above; panel C is another illustration of the clip/band; panel D illustrates a view of the band/clip without associated collars; panel E illustrates a view of the band/clip in the closed position.
Figure 8B:
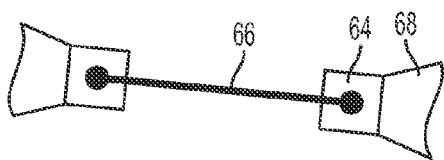
Figure 8C:
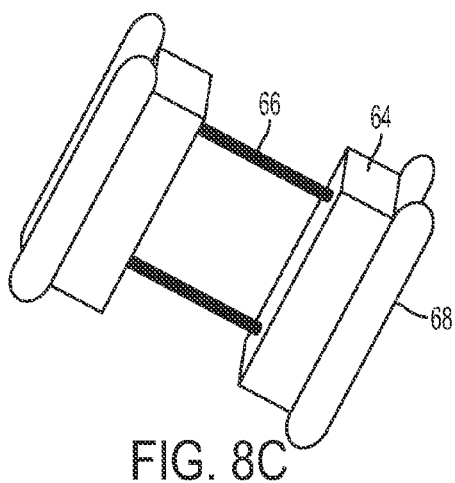
Figure 8D:
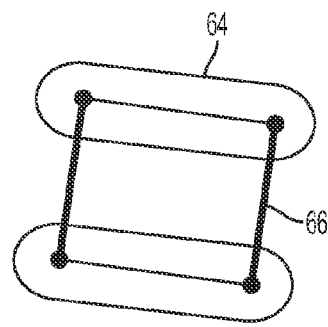
Figure 8E:
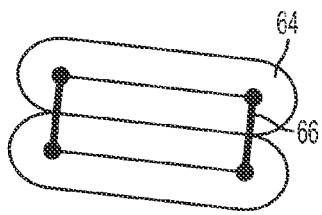

A similar configuration can be employed for a device that is used with a pericardial portal. Thus, shown in FIG. 7C is such a device 33, comprising a rectangular cylindrical container that has a proximal seal 35 surrounding a rod 37, or other type of access member that extends proximally for access by a user.

FIG. 8 demonstrates an embodiment of the linear band/clip for occlusion of an atrial appendage. The linear band/clip, may in alternate embodiments have two sides (64). The sides of the clip may be fashioned from a solid, or a semi-solid, or a flexible material such that the sides of the clip can be closed around an atrial appendage so as to occlude the atrial appendage from the rest of the atrium (FIG. 8A illustrates one side). FIGS. 8B-8E illustrate various views of the band/clip. FIGS. 8B-8D illustrate embodiments with the linear band/clip in the open position; FIG. 8E illustrates an embodiment with the band/clip closed. Also, FIGS. 8A-8C illustrate and embodiment wherein the band/clip is covered with a cloth collar (68); FIGS. 8D and 8E illustrate embodiments of the linear band/clip without the cloth collars (68).

In certain embodiments, the clip comprises solid sides (64), which have an incorporated elastic component (66) which can act as a band to exert a continuous circumferential closing force. The solid component (64) supports the linear band/clip structurally to equally distribute the closing force on the atrial appendage. This equal distribution can prevent bunching or placation of the appendage and may effectively encourage the sides of the non-circular appendage into opposition.

As noted above, in certain embodiments, a cloth collar(s) (68) may be attached to the linear band/clip provide rotational stability. Also, in certain embodiments, the cloth collar may be used to secure the band/clip to the distal end (22) (e.g., the inner circumference) of the portal (2). Thus, in certain embodiments, deployment of the clip and/or band around an atrial appendage may occur by removing a securing suture from the collar (68), thereby releasing the linear band/clip (62) from the portal (2).

In alternate embodiments, the elastic band and/or clip may have a diameter of about 1 to 5 cm, or 2 to 4 cm, about 3 cm. Also, in alternate embodiments, the solid clip component may have a length of about 1 to 10 cm, or 2 to 8 cm, or 3 to 7 cm, or 4 to 6 cm, or about 5 cm.

FIG. 9 demonstrates an embodiment of an oval AA portal comprising a flexible and/or collapsible distal end. In an embodiment, the distal end is oval; in this way, when the end of the portal is collapsed around the atrial appendage, the longer sides of the opening may flatten the AA while minimizing plication of the appendage. Or, in some cases, the distal end may be circular. Again, in certain embodiments (as described above but not shown in FIG. 9), the central lumen of the AA portal may be continuous with a side port which is connected to suction via a connector. In this way, when suction is applied to the side port, application of suction to the distal end of the AA portal can be controlled by occlusion of the opening to the side port. For example, when the opening to the side port is covered, the vacuum provided is applied to the distal end of the AA portal allowing for the AA portal to be securely positioned around an atrial appendage.

In certain embodiments, and as illustrated in FIG. 9A, the distal end (22) of the portal may be made of a pliable and collapsible material (e.g., plastic, silicone or the like). In certain embodiments, the distal end of the portal may be held open by a sliding bar (50). In certain embodiments, the sliding bar may be contained within a slot (52) positioned on the side of the portal. In an embodiments, there are a plurality of slots. For example, in an embodiment, there is a slot (52) and a sliding bar (50) on two sides of the portal (back slot not visible in FIG. 9A). As with the rectangular AA portal, both slots (52) may contain a sliding bar (50) which can be acted upon (i.e., urged distally and/or proximally) by moving a thumb bar (54) which is connected to a sliding bar (50) by a connecting bar (56). The distal end of the sliding bar (50) may divide into two (or more) separating bars (58a, 58b) which can be separated and forced apart by a fulcrum (60). When the thumb bar (54) is advanced distally, the sliding bar (50) may be advanced, pushing the separating bars (58a, 58b) against the fulcrum (60), thereby causing the bars (58a, 58b) to separate from each other and open the distal band/clip and, therefore, the distal end of the portal (22). This action can then hold the distal and pliable part of the portal (22) open. Or, other mechanisms for spreading (opening) the distal end of the portal may be used. In an embodiment, the atrial appendage may then be inserted into the open distal end of the AA portal.

FIG. 9B illustrates an oval portal (2) with the distal end in the closed position. In this configuration, the thumb bar (54) has been withdrawn proximally, retracting the sliding bar (50) and allowing the separating bars (58a, 58b) to come together and close the distal end of the portal (22). Also shown in FIGS. 9A and 9B is an oval clip/band (70) located at the distal end of the AA portal (2). In one embodiment depicted here, the oval band/clip is designed with intrinsic elastic properties which act to force the oval band/clip closed. The action at the thumb bar (54) opens and closes the oval band/clip (70). The oval band/clip (70), when in position, can be deployed and left in position at the appendage as the portal (2) is removed.

Figure 9C:
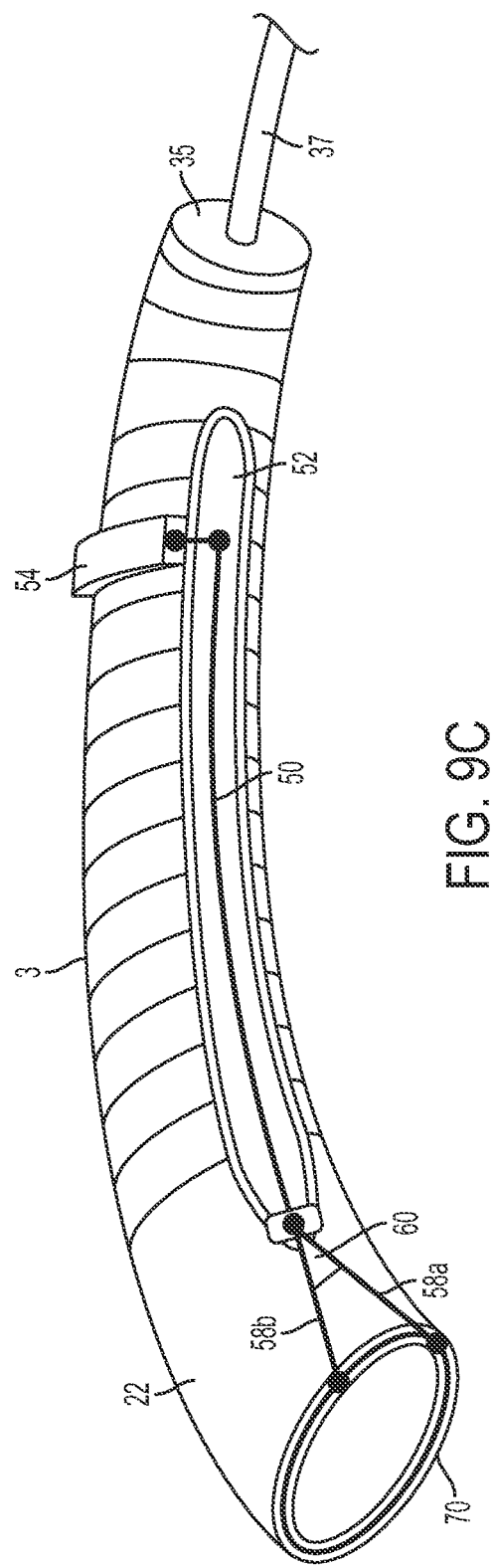
FIG. 9, panels A-C, illustrate an oval AA portal (panels A-B) or a device (panel C) used with a pericardial portal with an incorporated controllable release and deployment mechanism of the distal AA clip occlusion device in accordance with an embodiment of the present invention. Panels A and C illustrate the distal clip occlusion device in the open position; panel B illustrates the distal clip occlusion device in the closed position.

A similar configuration can be employed for a device that is used with a pericardial portal. Thus, shown in FIG. 9C is such a device 33, comprising an oval cylindrical container that has a proximal seal 35 surrounding a rod 37, or other type of access member that extends proximally for access by a user.

Figure 10A:
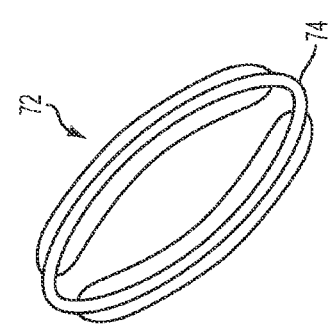
FIG. 10, panels A-E, illustrate an oval distal band/clip to be positioned at the distal end of the AA portal or a device used with a pericardial portal for occlusion of the appendage in accordance with an embodiment of the present invention. Panel A illustrates a view of the band/clip device; panel B illustrates the band/clip open; panel C is another illustration of the clip/band more open; panel D is another illustration of the clip/band open and with collars; panel E illustrates a view of the band/clip closed.
Figure 10B:
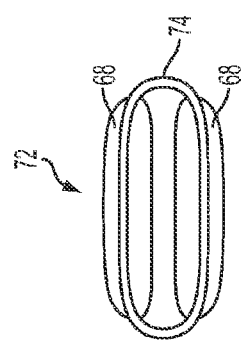
Figure 10C:
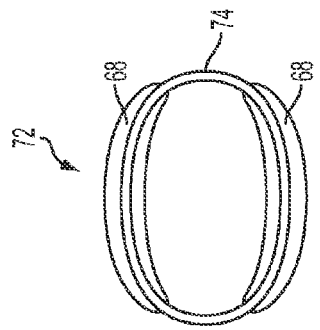
Figure 10D:
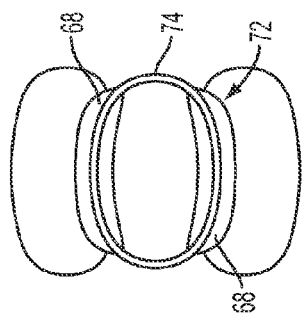
Figure 10E:
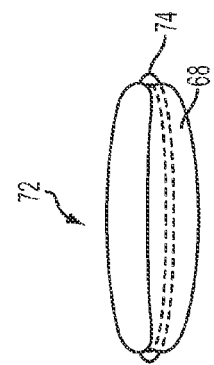

FIGS. 10A-10E demonstrates embodiments of an oval band/clip for occlusion of an appendage. The sides (72) of the clip may be fashioned from a solid, or a semi-solid, or a flexible material such that the sides of the clip can be closed around an atrial appendage so as to occlude the atrial appendage from the rest of the atrium FIGS. 10A-10E illustrate various views of the oval band/clip. FIGS. 10A-10D illustrate embodiments with the oval band/clip in the open position; FIG. 10E illustrates an embodiment with the oval band/clip closed. FIG. 10D illustrates and embodiment of the oval band/clip with the cloth collars (68).

In certain embodiments of the oval/circular clip, the solid sides (72) may have an incorporated elastic component (74) which acts as a band to exert a continuous circumferential closing force. The solid component (72) can support the oval band/clip structurally to equally distribute the closing force on the appendage. This equal distribution may prevent bunching or placation of the appendage and effectively encourages the sides of the non-circular appendage into opposition.

As noted with the rectangular clip, cloth collars (68) may be attached to the oval and/or circular band/clip provide rotational stability and to secure the band/clip to the distal end (22) of the portal (2).

Thus, in certain embodiments, deployment may occur by removing a securing suture from the collar (68), thereby releasing the oval band/clip (70) from the portal (2). In alternate embodiments, the elastic band component may have a diameter of about 1 to 5 cm, or 2 to 4 cm, about 3 cm. Also, in alternate embodiments, the solid clip component may have a length of about 1 to 10 cm, or 2 to 8 cm, or 3 to 7 cm, or 4 to 6 cm, or about 5 cm.

As noted herein, the clip or expandable elastic component may be selected from a variety of shapes. In certain embodiments, the clip and/or band is shaped to have at least one longer sides and two shorter sides such that when the clip and/or band is closed around the atrial appendage, the longer sides flatten the appendage in a manner so as to substantially avoid plication of the appendage. For example, clips that are oval, rectangular, diamond-shaped or the like may be used.

FIG. 11, panels A-D, illustrates clips positioned around an atrial appendage in accordance with various embodiments of the invention. Thus, FIGS. 11A and 11B show an oval distal band/clip having an elastic component (74) and flexible sides (72) positioned around an atrial appendage (24) emanating from the atrial surface (46) where FIG. 11A shows the clip open, and FIG. 11B shows the clip closed around the atrial appendage. FIG. 11C and 11D shows a diamond-shaped clip having an elastic component (74) and flexible sides (72) positioned around an atrial appendage (24) emanating from the atrial surface (46) where FIG. 11C shows the clip open, and FIG. 11D shows the clip closed around the atrial appendage.

All publications and patent applications cited herein are incorporated by reference in their entireties. This application incorporates by reference herein in their entireties U.S. patent application Ser. No. 12/642,137, entitled "Methods and Devices for Endoscopic Access to the Heart" and filed Dec. 18, 2009, U.S. patent application Ser. No. 12/456,855 entitled "Endoscopic Cardiac and Thoracic Surgical Devices and Systems and Methods of Use of Such Devices and Systems" filed on Jun. 23, 2009, U.S. Provisional Patent Application 61/135,260, filed on Jul. 19, 2008, and entitled "Totally Endoscopic Cardiac and Thoracic Surgical Devices and Methods," and U.S. Provisional Patent Application 61/191,062, filed on Sep. 6, 2008, entitled "Pericardial and Extrapericardial Surgical Devices and Methods."

That which is claimed is:

1. A device for performing a surgical procedure on an atrial appendage via a pericardial approach, wherein the device is configured for insertion of atrial appendage tissue therein, wherein the device is configured to exclude and/or remove the atrial appendage from an atrium to which the appendage is attached, and wherein at least a portion of a distal end of the device is curvilinear such that the distal end of the device is not parallel to a longitudinal axis of the device.

2. The device of claim 1, comprising a portal, the portal comprising a proximal end having an opening and a distal end having an opening and a lumen connecting the proximal and distal openings, wherein the distal end opening of the portal is configured for the insertion of the atrial appendage tissue.

3. The device of claim 1, wherein the device is configured to be inserted into a pericardial portal, the pericardial portal comprising a proximal end having an opening and a distal end having an opening and a lumen connecting the proximal and distal openings.

4. The device of claim 1, further comprising an endoscope.

5. The device of claim 1, wherein suction can be applied to create a seal between at least a portion of a distal opening of the device and at least part of the atrial appendage.

6. The device of claim 1, comprising a soft material at the distal end of the device.

7. The device of claim 1, wherein the device comprises a tying band configured to be tied around a portion of the atrial appendage.

8. The device of claim 7, wherein at least a portion of the tying band comprises a material designed to cushion the tying band.

9. The device of claim 1, wherein the device comprises an expandable and/or contractible band positioned on or near the distal end of the device.

10. The device of claim 1, further comprising an inflatable member positioned on the distal end of the device.

11. The device of claim 10, further comprising a lumen configured to inflate the inflatable member.

12. The device of claim 10, wherein an expandable and/or contractible band is positioned proximal to the inflatable member such that when the inflatable member is inflated, the band is secured on the distal end of the device, and when the inflatable member is deflated, the band can be urged over the deflated inflatable member so as to be released from the distal end of the device.

13. The device of claim 10, wherein an expandable and/or contractible band is positioned substantially on top of the inflatable member, such that when the inflatable member is deflated, the band is secured on the distal end of the device, and when the inflatable member is inflated, the band is pushed off the distal end of the device.

14. The device of claim 1, wherein the distal end of the device is sufficiently flexible so as to be collapsed around the atrial appendage.

15. The device of claim 14, further comprising a clip and/or band positioned at the distal end of the device which may be positioned around the atrial appendage so as to occlude the atrial appendage from the atrium.

16. The device of claim 15, wherein the clip and/or band is shaped to have at least two longer sides and two shorter sides such that when the clip and/or band is closed around the atrial appendage, the longer sides flatten the appendage in a manner so as to substantially avoid plication of the appendage.

17. The device of claim 15, wherein the clip and/or band is oval, rectangular or diamond in shape.

18. The device of claim 15, wherein the distal end is shaped to collapse around the atrial appendage without the application of force.

19. The device of claim 18, wherein the device comprises a mechanism to open the distal end of the device.

20. The device of claim 19, wherein the mechanism to open the distal end of the device comprises at least one bar that when urged distally, pushes the distal end of the device from a naturally closed configuration to an open configuration.

21. The device of claim 15, wherein the clip and/or band is releasably engaged with the distal end, such that when the clip and/or band is collapsed around the atrial appendage, the clip and/or band may be released from the distal end of the device so as to collapse around at least a portion of the atrial appendage.

22. The device of claim 1, configured specifically to access either the left atrial appendage or the right atrial appendage.

23. The device of claim 1, wherein the device is configured to exclude and remove the atrial appendage from the atrium.

24. The device of claim 1, wherein the device is configured to exclude or remove the atrial appendage from the atrium.

25. The device of claim 1, wherein the device is configured to exclude the atrial appendage from the atrium.

26. The device of claim 1, wherein the device is configured to remove the atrial appendage from the atrium.

27. A method to access an atrial appendage of a heart in a subject via a pericardial approach so as to perform a surgical procedure upon the atrial appendage, the method comprising:
   (a) inserting a device into the pericardium of the subject, wherein the device is configured for insertion of atrial appendage tissue therein, and wherein the device is configured to exclude and/or remove the atrial appendage from an atrium to which the appendage is attached, and wherein the device comprises a portal comprising a proximal end having an opening and a distal end having an opening and a lumen connecting the proximal and distal openings;
   (b) manipulating the proximal end of the portal to position the distal opening of the portal at or near the surface of the atrium; and
   (c) inserting at least a portion of the atrial appendage into the device; and
   (d) applying a vacuum to the lumen of the portal to encourage the atrial appendage into the device and/or to create a seal between the distal opening of the portal and at least part of the atrial appendage.

28. The method of claim 27, wherein the portal comprises an atrial appendage portal, wherein the distal end is configured for insertion of the atrial appendage tissue therein.

29. The method of claim 27, further comprising inserting the device and/or the portal into an outer pericardial portal and positioning the distal opening of the portal at the surface of the atrium.

30. The method of claim 27, wherein at least a portion of the distal end of the device and/or the portal is curvilinear such that the distal opening is not parallel to a longitudinal axis of the device.

31. The method of claim 27, further comprising using an endoscope to provide an image of body structures present near the distal end of the portal.

32. The method of claim 27, wherein the portal and/or the device comprises a soft material surrounding the distal end of the portal and/or a distal end of the device.

33. The method of claim 27, wherein the device comprises a tying band configured to be tied around a portion of the atrial appendage.

34. The method of claim 33, wherein the tying band comprises a suture, and at least a portion of the suture comprises a material designed to cushion the suture.

35. The method of claim 33, further comprising providing the tying band at the distal opening of the portal, using the tying band to encircle at least a portion of the atrial appendage, and tightening the tying band around the atrial appendage to exclude the atrial appendage from the atrium to which the appendage is attached.

36. The method of claim 27, wherein the device comprises an expandable and/or contractible band and/or clip positioned on or near the distal end of the portal and/or a distal end of the device.

37. The method of claim 36, further comprising using an inflatable member to secure the expandable and/or contractible band and/or clip on the distal end of the portal and/or the distal end of the device.

38. The method of claim 37, comprising positioning the expandable and/or contractible band proximal to the inflatable member, and deflating the inflatable member to release the expandable and/or contractible band and/or clip from the distal end of the portal and/or the distal end of the device.

39. The method of claim 37, comprising positioning the expandable and/or contractible band or clip substantially on top of the inflatable member, and inflating the inflatable member to urge the expandable and/or contractible band and/or clip from the distal end of the portal and/or the distal end of the device.

40. The method of claim 36, further comprising removing the expandable and/or contractible band and/or clip from the distal end of the portal and/or the distal end of the device and positioning the expandable and/or contractible band and/or clip on the atrial appendage so as to encircle at least a portion of the atrial appendage to exclude the atrial appendage from the atrium to which the appendage is attached.

41. The method of claim 36, wherein the expandable and/or contractible band and/or clip is configured to close around the atrial appendage upon emplacement of the clip and/or band on the atrial appendage.

42. The method of claim 36, wherein the expandable and/or contractible band and/or clip is releasably secured to the device.

43. The method of claim 42, further comprising using a suture to releasably secure the expandable and/or contractible band and/or clip to the device and then cutting the suture to release the expandable and/or contractible band and/or clip from the device.

44. The method of claim 36, wherein the clip and/or band is shaped to have at least two longer sides and two shorter sides such that when the clip and/or band is closed around the atrial appendage, the longer sides flatten the appendage in a manner so as to substantially avoid plication of the appendage.

45. The method of claim 36, wherein the clip or band is oval, rectangular or diamond in shape.

46. The method of claim 27, wherein a distal end of the device and/or the distal end of the portal is configured to be collapsible around the atrial appendage.

47. The method of claim 46, wherein the distal end of the portal is shaped to collapse around the atrial appendage without the application of force.

48. The method of claim 46, wherein the portal and/or the device comprises a mechanism to open the distal end of the portal and/or the distal end of device.

49. The method of claim 48, wherein the mechanism to open the distal end of the portal and/or the distal end of the device comprises at least one bar that when urged distally, pushes the distal end of the portal and/or the device from a naturally closed configuration to an open configuration.

50. The method of claim 36, wherein the clip and/or band is releasably engaged with the distal end of the portal and/or the distal end of the device, such that when the clip and/or band is collapsed around an atrial appendage, the clip or band may be released from the distal end of the portal and/or the distal end of the device so as to collapse around at least a portion of the atrial appendage.

51. The method of claim 27, wherein the portal and/or the device is configured specifically to access either the left atrial appendage or the right atrial appendage.

52. The method of claim 27, wherein the portal and/or the device comprises a collapsible distal end with a clip and/or band that can be positioned in the distal end of the portal and/or the distal end of the device and then allowed to collapse around the atrial appendage and comprising the steps of
using suction to positioning the atrial appendage in the distal end of the portal and/or the distal end of the device;
collapsing the distal end of the portal and/or the distal end of the device and associated clip and/or band around the atrial appendage; and
releasing the clip and/or band from the portal and/or the device so as to be left on the atrial appendage when the portal is removed.

53. A device for performing a surgical procedure on an atrial appendage via a pericardial approach, wherein the device is configured for insertion of atrial appendage tissue therein, wherein the device is configured to exclude and/or remove the atrial appendage from an atrium to which the appendage is attached, and wherein suction can be applied to create a seal between at least a portion of a distal opening of the device and at least part of the atrial appendage.

54. A device for performing a surgical procedure on an atrial appendage via a pericardial approach, wherein the device is configured for insertion of atrial appendage tissue therein, wherein the device is configured to exclude and/or remove the atrial appendage from an atrium to which the appendage is attached, and wherein the device comprises a soft material at a distal end of the device.

55. A device for performing a surgical procedure on an atrial appendage via a pericardial approach, wherein the device is configured for insertion of atrial appendage tissue therein, wherein the device is configured to exclude and/or remove the atrial appendage from an atrium to which the appendage is attached, and wherein the device comprises a tying band configured to be tied around a portion of the atrial appendage.

56. A method to access an atrial appendage of a heart in a subject via a pericardial approach so as to perform a surgical procedure upon the atrial appendage, the method comprising:
(a) inserting a device into the pericardium of the subject, wherein the device is configured for insertion of atrial appendage tissue therein, and wherein the device is configured to exclude and/or remove the atrial appendage from an atrium to which the appendage is attached, and wherein the device comprises a portal comprising a proximal end having an opening and a distal end having an opening and a lumen connecting the proximal and distal openings;
(b) manipulating the proximal end of the portal to position the distal opening of the portal at or near the surface of the atrium; and
(c) inserting at least a portion of the atrial appendage into the device,
wherein at least a portion of a distal end of the device and/or the portal is curvilinear such that the distal opening is not parallel to a longitudinal axis of the device.

57. A method to access an atrial appendage of a heart in a subject via a pericardial approach so as to perform a surgical procedure upon the atrial appendage, the method comprising:
(a) inserting a device into the pericardium of the subject, wherein the device is configured for insertion of atrial appendage tissue therein, and wherein the device is configured to exclude and/or remove the atrial appendage from an atrium to which the appendage is attached, and wherein the device comprises a portal comprising a proximal end having an opening and a distal end having an opening and a lumen connecting the proximal and distal openings,
(b) manipulating the proximal end of the portal to position the distal opening of the portal at or near the surface of the atrium; and
(c) inserting at least a portion of the atrial appendage into the device,
wherein the portal and/or the device comprises a soft material surrounding the distal end of the portal and/or a distal end of the device.

58. A method to access an atrial appendage of a heart in a subject via a pericardial approach so as to perform a surgical procedure upon the atrial appendage, the method comprising:
(a) inserting a device into the pericardium of the subject, wherein the device is configured for insertion of atrial appendage tissue therein, and wherein the device is configured to exclude and/or remove the atrial appendage from an atrium to which the appendage is attached, and wherein the device comprises a portal comprising a proximal end having an opening and a distal end having an opening and a lumen connecting the proximal and distal openings,
(b) manipulating the proximal end of the portal to position the distal opening of the portal at or near the surface of the atrium; and
(c) inserting at least a portion of the atrial appendage into the device, wherein the device comprises a tying band configured to be tied around a portion of the atrial appendage.

59. A method to access an atrial appendage of a heart in a subject via a pericardial approach so as to perform a surgical procedure upon the atrial appendage, the method comprising:
  (a) inserting a device into the pericardium of the subject, wherein the device is configured for insertion of atrial appendage tissue therein, and wherein the device is configured to exclude and/or remove the atrial appendage from an atrium to which the appendage is attached, and wherein the device comprises a portal comprising a proximal end having an opening and a distal end having an opening and a lumen connecting the proximal and distal openings,
  (b) manipulating the proximal end of the portal to position the distal opening of the portal at or near the surface of the atrium; and
  (c) inserting at least a portion of the atrial appendage into the device, wherein the portal and/or the device comprises a collapsible distal end with a clip and/or band that can be positioned in the distal end of the portal and/or the distal end of the device and then allowed to collapse around an atrial appendage, and wherein the method further comprises:
  using suction to position the atrial appendage in the distal end of the portal and/or the distal end of the device;
  collapsing the distal end of the portal and/or the distal end of the device and associated clip and/or band around the atrial appendage; and
  releasing the clip and/or band from the portal and/or the device so as to be left on the atrial appendage when the portal is removed.

\* \* \* \* \*

UNITED STATES PATENT AND TRADEMARK OFFICE
CERTIFICATE OF CORRECTION

PATENT NO. : 8,814,778 B2  
APPLICATION NO. : 13/151403  
DATED : August 26, 2014  
INVENTOR(S) : Andy Christopher Kiser et al.

Page 1 of 1

It is certified that error appears in the above-identified patent and that said Letters Patent is hereby corrected as shown below:

In the Claims,

Column 23, line 67, please delete "and".

Signed and Sealed this
Sixteenth Day of December, 2014

Michelle K. Lee
*Deputy Director of the United States Patent and Trademark Office*